(12) United States Patent
Sangu

(10) Patent No.: US 11,435,322 B2
(45) Date of Patent: Sep. 6, 2022

(54) OBJECTIVE OPTICAL SYSTEM AND PHOTOACOUSTIC IMAGING DEVICE

(71) Applicant: YOKOGAWA ELECTRIC CORPORATION, Musashino (JP)

(72) Inventor: Hiroyuki Sangu, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 304 days.

(21) Appl. No.: 16/623,135

(22) PCT Filed: Mar. 28, 2018

(86) PCT No.: PCT/JP2018/012867
§ 371 (c)(1),
(2) Date: Dec. 16, 2019

(87) PCT Pub. No.: WO2018/235377
PCT Pub. Date: Dec. 27, 2018

(65) Prior Publication Data
US 2020/0173965 A1 Jun. 4, 2020

(30) Foreign Application Priority Data

Jun. 19, 2017 (JP) .............................. JP2017-119677
Feb. 16, 2018 (JP) .............................. JP2018-025937

(51) Int. Cl.
*G01N 29/24* (2006.01)
*G01N 21/64* (2006.01)
(Continued)

(52) U.S. Cl.
CPC ......... *G01N 29/2418* (2013.01); *G01N 21/64* (2013.01); *G01N 29/02* (2013.01); *G02B 17/061* (2013.01)

(58) Field of Classification Search
CPC .... G01N 29/2418; G01N 29/02; G01N 21/00; G01N 21/64; A61B 5/7425; A61B 5/0071; A61B 5/0095
See application file for complete search history.

(56) References Cited

U.S. PATENT DOCUMENTS 5,469,744 A * 11/1995 Patton .................... G01N 29/28
73/644
5,999,836 A * 12/1999 Nelson ................ A61B 5/0091
250/339.02
(Continued)

FOREIGN PATENT DOCUMENTS

CN 105548022 A * 5/2016
JP 2009-115830 A 5/2009
(Continued)

OTHER PUBLICATIONS

International Search Report dated Jun. 26, 2018 in No. PCT/JP2018/012867 3 pages.
(Continued)

*Primary Examiner* — Tarun Sinha
(74) *Attorney, Agent, or Firm* — Rankin, Hill & Clark LLP

(57) ABSTRACT

An object of the present invention is to provide an objective optical system and a photoacoustic imaging apparatus capable of obtaining a clearer image of a sample than before. The objective optical system (23) includes: a convex mirror (101) having a convex reflecting surface for reflecting pulsed light traveling toward a sample (SP); a concave mirror (102) having a concave reflecting surface for reflecting the light reflected by the convex mirror (101) and irradiating the sample (SP) with the light; and an ultrasonic detector (103) having at least one end portion provided on an object side of the convex mirror (101), and detecting an
(Continued)

acoustic wave obtained by irradiating the sample (SP) with the light.

20 Claims, 13 Drawing Sheets

(51) Int. Cl.
*G01N 29/02* (2006.01)
*G02B 17/06* (2006.01)

(56) References Cited

U.S. PATENT DOCUMENTS

| | | |
|---|---|---|
| 2010/0268042 A1 | 10/2010 | Wang et al. |
| 2011/0275890 A1 | 11/2011 | Wang et al. |
| 2013/0134310 A1 | 5/2013 | Furstenberg et al. |
| 2016/0220120 A1* | 8/2016 | Kim .................. A61B 5/0066 |
| 2017/0356884 A1* | 12/2017 | Hu ......................... G01N 29/28 |
| 2017/0371139 A1 | 12/2017 | Ueda |
| 2018/0140199 A1 | 5/2018 | Sangu |

FOREIGN PATENT DOCUMENTS

| | | |
|---|---|---|
| JP | 2015-062678 A | 4/2015 |
| JP | 2016-202631 A | 12/2016 |
| WO | 2013/078471 A1 | 5/2013 |
| WO | 2016-094434 A1 | 6/2016 |
| WO | 2016/110935 A1 | 7/2016 |

OTHER PUBLICATIONS

Hui Wang et al., "Reflection-mode optical-resolution photoacoustic microscopy based on a reflective objective", Optics Express vol. 21, No. 20, p. 24210-24218, Oct. 2013; Cited in Specification.

Junjie Yao et al., "Sensitivity of photoacoustic microscopy", Photoacoustics vol. 2, Issue 2, Jun. 2014, p. 87-101; Cited in Specification.

Rui Cao et al., "Multispectral photoacoustic microscopy based on an optical-acoustic objective", Photoacoustics vol. 3, Issue 2, Jun. 2015, p. 55-59; Cited in Specification.

\* cited by examiner

OBJECTIVE OPTICAL SYSTEM AND PHOTOACOUSTIC IMAGING DEVICE

TECHNICAL FIELD

The present invention relates to an objective optical system and a photoacoustic imaging apparatus.

BACKGROUND ART

In recent years, photoacoustic imaging that can image a sample of a living tissue, organ, cell or the like into a two-dimensional image or a three-dimensional image without using a dye, a label or the like has attracted attention. The photoacoustic imaging is a technique for imaging the sample based on an acoustic wave obtained from the sample when the sample is irradiated with a short pulse laser by using a photoacoustic effect (a phenomenon in which the acoustic wave is generated due to thermoelastic expansion caused by absorption of light energy by the sample). Here, since the acoustic wave generated in the sample is less attenuated in the sample, a deep part of the sample can also be imaged in the photoacoustic imaging.

Examples of conventional photoacoustic imaging apparatuses are disclosed in PATENT LITERATURES 1 to 3 and NON-PATENT LITERATURES 1 to 3 below. For example, the photoacoustic imaging apparatus disclosed in the following PATENT LITERATURE 1 uses a confocal photoacoustic microscope system, and includes a laser that generates a light pulse, and a focusing assembly that focuses the light pulse on a region inside an object, an ultrasonic transducer that receives sound waves emitted from the object, and an electronic system that processes the sound waves to generate an image of the region inside the object. Here, the focusing assembly includes a separating member (a member in which a silicon oil layer is provided between two prisms) disposed on the object side of an objective lens, and the light pulse and an acoustic signal are separated by the separating member.

CITATION LIST

Patent Literature

PATENT LITERATURE 1: JP-A-2015-062678
PATENT LITERATURE 2: JP-A-2016-202631
PATENT LITERATURE 3: WO 2016/094434

Non-Patent Literature

NON-PATENT LITERATURE 1: Hui Wang et al., "Reflection-mode optical-resolution photoacoustic microscopy based on a reflective objective", Optics Express Vol. 21, No. 20, p. 24210-24218
NON-PATENT LITERATURE 2: Junjie Yao et al., "Sensitivity of photoacoustic microscopy", Photoacoustics Volume 2, Issue 2, June 2014, p. 87-101
NON-PATENT LITERATURE 3: Rui Cao et al., "Multispectral photoacoustic microscopy based on an optical-acoustic objective", Photoacoustics Volume 3, Issue 2, June 2015, p. 55-59

SUMMARY OF THE INVENTION

Problems to be Solved by the Invention

By the way, since the photoacoustic imaging apparatus disclosed in PATENT LITERATURE 1 described above separates the light pulse and the acoustic signal by the separating member disposed on the object side of the objective lens, a distance between the objective lens and the sample inevitably increases. Further, in the photoacoustic imaging apparatus disclosed in PATENT LITERATURE 1 described above, the acoustic wave generated in the sample passes through various members (for example, a prism and an acoustic lens constituting the separating member) before being guided to a detector (an ultrasonic transducer).

Therefore, in the photoacoustic imaging apparatus disclosed in PATENT LITERATURE 1 described above, there is a possibility that the acoustic wave generated in the sample is attenuated before it is detected by the detector, and a signal intensity of the acoustic wave detected by the detector is reduced. Further, there is also a possibility that aberrations may occur in a configuration of the photoacoustic imaging apparatus disclosed in PATENT LITERATURE 1 described above. If there is such attenuation or aberration of the acoustic wave, for example, there is a possibility that the image of the sample is unclear.

In the photoacoustic imaging apparatus, in order to improve resolution, it is necessary to use, for example, the objective lens having a large numerical aperture (NA). However, since the objective lens having a large numerical aperture has a short working distance, it is difficult to use in a configuration in which the separating member is provided on the object side of the objective lens as in the photoacoustic imaging apparatus disclosed in PATENT LITERATURE 1 described above, and there is a problem that it is difficult to improve the resolution.

The present invention has been made in view of the above circumstances, and an object of the present invention is to provide the objective optical system and the photoacoustic imaging apparatus capable of obtaining a clearer image of the sample than before.

Solution to the Problems

In order to solve the above problems, an objective optical system (23, 23A to 23D, 53, 53A) of the present invention includes: a first mirror (101) having a convex reflecting surface for reflecting light traveling toward a sample (SP); a second mirror (102) having a concave reflecting surface for reflecting the light reflected by the first mirror and irradiating the sample with the light; and a detector (103) having at least one end portion provided on an object side of the first mirror, and detecting an acoustic wave obtained by irradiating the sample with the light.

In the objective optical system of the present invention, a hole portion (H) through which the light traveling toward the sample passes is formed in a central portion of the second mirror, and the first mirror, the second mirror, and the detector are arranged in an order of the second mirror, the first mirror, and the one end portion of the detector on an optical axis (AX) of the light traveling toward the sample.

In the objective optical system of the present invention, the detector is rod-shaped, and a hole portion (h) through which the detector is to be inserted is formed in a central portion of the first mirror.

In the objective optical system of the present invention, the detector is disposed outside an optical path of the light irradiated to the sample so as not to block the light irradiated to the sample.

In the objective optical system of the present invention, the detector includes an acoustic lens (103A) for collecting the acoustic wave obtained by irradiating the sample with the light.

The objective optical system of the present invention includes a transparent cover member (105) that is provided on the object side of the first mirror and the second mirror, forms a boundary surface with liquid, and prevents the liquid from entering the first mirror and the second mirror.

In the objective optical system of the present invention, the detector is fixed to the object side of the cover member, and the first mirror is provided on an opposite side to the object side of the cover member.

In the objective optical system of the present invention, at least one of a light incident surface (105a) and a light exit surface (105b) of the cover member is formed in a substantially spherical surface, and a center of curvature of the spherical surface is substantially equal to a focal position (P) of a reflective optical system formed by the first mirror and the second mirror.

In the objective optical system of the present invention, an optical path in which the light reflected by the second mirror reaches the sample or a container (CT1) of the sample is filled with liquid.

The objective optical system of the present invention includes an optical member (200) having a first surface (200a) in which the first mirror is formed in a central portion thereof, and a transmissive portion (TS) is provided in a peripheral portion thereof, and a second surface (200b) in which the light traveling toward the sample is incident on a central portion thereof, and the second mirror is formed in a peripheral portion thereof, wherein the detector is fixed to a central portion on the object side of the optical member.

In the objective optical system of the present invention, the transmissive portion is formed in a substantially spherical surface, and a center of curvature of the spherical surface is substantially equal to a focal position (P) of a reflective optical system formed by the first mirror and the second mirror.

The objective optical system of the present invention includes: a lens barrel (100) for supporting at least the second mirror therein; and a tubular liquid holding member (106, 110) that is provided so that one end portion thereof surrounds a periphery of the object side of the lens barrel and can hold liquid (WT, CF) therein.

The objective optical system of the present invention includes a liquid conduit (111, 121, 201) for introducing the liquid into the liquid holding member.

In the objective optical system of the present invention, a bottom portion of the container (CT1) of the sample is disposed close to the other end portion of the liquid holding member, and a space between the liquid holding member and the bottom portion of the container is filled with the liquid (WT) held inside the liquid holding member.

In the objective optical system of the present invention, the liquid holding member is a tubular member having a diameter reduced from the one end portion to the other end portion.

A photoacoustic imaging apparatus of the present invention is a photoacoustic imaging apparatus (1, 2) for generating an image of a sample based on an acoustic wave obtained by irradiating the sample with light, including an objective optical system (23, 23A to 23D, 53, 53A) according to any one of the above, that irradiates the sample with light and detects the acoustic wave obtained by irradiating the sample with the light.

The photoacoustic imaging apparatus of the present invention includes a scanning optical unit (13) for scanning the light irradiated to the sample, wherein a pupil position of the objective optical system is optically conjugated with inside or vicinity of the scanning optical unit.

In the photoacoustic imaging apparatus of the present invention, the pupil position of the objective optical system is a position of the first mirror.

The photoacoustic imaging apparatus of the present invention includes an optical system (19) for converting light incident on the objective optical system into the light having a ring-shaped cross-section.

In the photoacoustic imaging apparatus of the present invention, the optical system is configured by using two axicon lenses (19a, 19b) arranged so that apex angles thereof are opposed to each other.

The photoacoustic imaging apparatus of the present invention further includes: a photodetector (18) for detecting fluorescence obtained by irradiating the sample with the light; and an image generator (30) for generating a photoacoustic image based on a detection result of the acoustic wave and generating a fluorescence image based on a detection result of the photodetector.

Effects of the Invention

According to the present invention, by using the objective optical system including: a first mirror having a convex reflecting surface for reflecting light traveling toward a sample; a second mirror having a concave reflecting surface for reflecting the light reflected by the first mirror and irradiating the sample with the light; and a detector having at least one end portion provided on an object side of the first mirror, and detecting an acoustic wave obtained by irradiating the sample with the light, since the objective optical system can be disposed close to the sample, there is an effect that it is possible to obtain a clearer sample image (image based on the acoustic wave obtained from the sample) than before.

DESCRIPTION OF THE EMBODIMENTS

Figure 1:
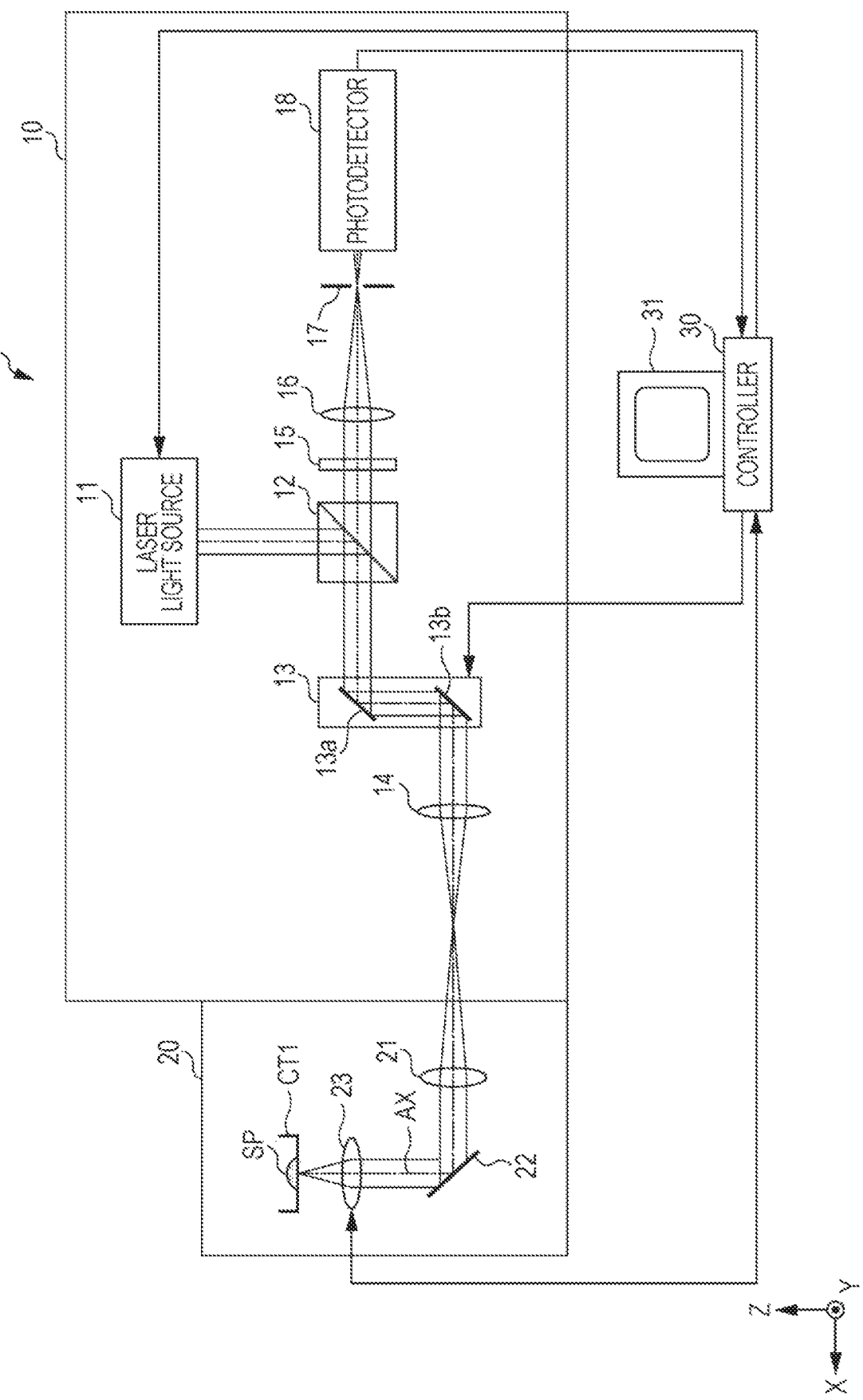
FIG. 1 is a diagram showing a main configuration of a photoacoustic imaging apparatus according to a first embodiment of the present invention.

An objective optical system and a photoacoustic imaging apparatus according to embodiments of the present invention will be described in detail with reference to the drawings below. In the drawings referred to below, dimensions of members are appropriately changed as necessary for easy understanding. In the following, positional relationship between members will be described with reference to an XYZ orthogonal coordinate system set in the drawing as necessary. In the XYZ orthogonal coordinate system, an X axis and a Y axis are set in a horizontal plane, and a Z axis is set in a vertical direction. However, for convenience of explanation, origin of the XYZ orthogonal coordinate system shown in the drawings is not fixed, and its position is changed as appropriate for each of the drawings.

First Embodiment

<Photoacoustic Imaging Apparatus>

FIG. 1 is a diagram showing a main configuration of the photoacoustic imaging apparatus according to a first embodiment of the present invention. As shown in FIG. 1, a photoacoustic imaging apparatus 1 of the present embodiment includes a confocal unit 10, an inverted microscope 20, and a controller 30 (image generator), and generates an image of a sample SP based on an acoustic wave or fluorescence obtained by irradiating pulsed laser light (hereinafter referred to as pulsed light) on the sample SP stored in a sample container CT1. Hereinafter, the image based on the acoustic wave obtained from the sample SP is referred to as a "photoacoustic image", and the image based on the fluorescence obtained from the sample SP is referred to as a "fluorescence image".

The confocal unit 10 is a unit forming a main portion of a confocal microscope. The confocal microscope is realized by attaching the inverted microscope 20 to the confocal unit 10. Note that not only the inverted microscope 20 can be attached to the confocal unit 10, but other microscopes (for example, an upright microscope) can also be attached thereto. That is, an arbitrary microscope can be attached to the confocal unit 10 according to an application of the confocal microscope.

The confocal unit 10 includes a laser light source 11, a dichroic mirror 12, a scanning optical unit 13, a pupil projection lens 14, a fluorescence filter 15, a lens 16, a pinhole 17, and a photodetector 18. The laser light source 11 emits the pulsed light for irradiating the sample SP stored in the sample container CT1 under control of the controller 30. A wavelength of the pulsed light emitted from the laser light source 11 can be set to an arbitrary wavelength depending on the sample SP. Further, the laser light source 11 may be capable of changing the wavelength continuously or discretely.

The dichroic mirror 12 is a mirror that reflects the light having the wavelength of the pulsed light emitted from the laser light source 11 and transmits the light having a wavelength of the fluorescence obtained from the sample SP. The dichroic mirror 12 is disposed on a −Z side of the laser light source 11, and reflects the pulsed light emitted in a −Z direction from the laser light source 11 in a +X direction, to transmit the fluorescence emitted from the scanning optical unit 13 and traveling in a −X direction.

The scanning optical unit 13 is a unit for scanning the pulsed light irradiated to the sample SP in a plane orthogonal to an optical axis AX under the control of the controller 30. Specifically, the scanning optical unit 13 includes a variable mirror 13a that reflects the pulsed light reflected in the +X direction by the dichroic mirror 12 in the −Z direction, and a variable mirror 13b that reflects the pulsed light reflected in the −Z direction by the variable mirror 13a in the +X direction. The variable mirrors 13a and 13b are configured to be rotatable about axes orthogonal to each other. For example, the variable mirror 13a is configured to be rotatable about an axis parallel to the Y axis, and the variable mirror 13b is configured to be rotatable around an axis, which is included in a ZX plane and along a reflecting surface of the variable mirror 13b. Rotations of the variable mirrors 13a and 13b are controlled by the controller 30.

The pupil projection lens 14 is disposed on a +X side of the variable mirror 13b provided in the scanning optical unit 13, collects the pulsed light reflected in the +X direction by the variable mirror 13b, and converts the fluorescence emitted in the −X direction from the inverted microscope 20 into parallel light. In an example shown in FIG. 1, the pulsed light is collected in the confocal unit 10 by the pupil projection lens 14, and the diverging pulsed light is emitted from the confocal unit 10. Note that the pulsed light (diverging pulsed light) emitted from the confocal unit 10 is incident on the inverted microscope 20.

The fluorescence filter 15 is disposed on the −X side of the dichroic mirror 12 and selectively transmits the fluorescence obtained from the sample SP. The lens 16 collects the fluorescence that has transmitted through the fluorescence filter 15. The pinhole 17 is disposed at a focal position (focal position on the −X side) of the lens 16. The photodetector 18 is disposed on the −X side of the pinhole 17 and detects the light that has passed through the pinhole 17. A detection signal of the photodetector 18 is output to the controller 30.

The inverted microscope 20 includes an imaging lens 21, a mirror 22, and an objective optical system 23, and observes the sample SP stored in the sample container CT1 from a lower side (the −Z side). The imaging lens 21 is a lens that converts the pulsed light emitted from the confocal unit 10 and incident on the inverted microscope 20 into parallel light, and forms an image of the fluorescence reflected by the mirror 22 and traveling in the −X direction. The mirror 22 is disposed in the +X direction of the imaging lens 21, reflects the pulsed light traveling in the +X direction through the imaging lens 21 in a +Z direction, and reflects the fluorescence traveling in the −Z direction through objective optical system 23 in the −X direction.

The objective optical system 23 is disposed on the +Z side of the mirror 22, collects the pulsed light reflected in the +Z direction by the mirror 22 to irradiate the sample SP with the light, and converts the fluorescence obtained from the sample SP into parallel light. Further, the objective optical system 23 detects the acoustic wave obtained by irradiating the sample SP with pulsed light. A detection signal of the objective optical system 23 is output to the controller 30. The objective optical system 23 is configured to be movable in the Z direction under the control of the controller 30. Details of the objective optical system 23 will be described below.

The controller 30 controls operation of the photoacoustic imaging apparatus 1 in an integrated manner. For example, the laser light source 11 provided in the confocal unit 10 is controlled to emit or stop the pulsed light irradiated to the sample SP. Further, the scanning optical unit 13 provided in the confocal unit 10 and the objective optical system 23 provided in the inverted microscope 20 are controlled to scan the sample SP with the pulsed light (X-axis, Y-axis, and Z-axis scanning). Further, the controller 30 performs signal processing of the detection signal output from the photodetector 18 provided in the confocal unit 10 to generate a fluorescence image and display it on a display monitor 31, and performs signal processing of the detection signal output from the objective optical system 23 to generate the photoacoustic image and display it on the display monitor 31. The display monitor 31 is a monitor provided with, for example, a liquid crystal display device.

<Objective Optical System>

Figure 2:
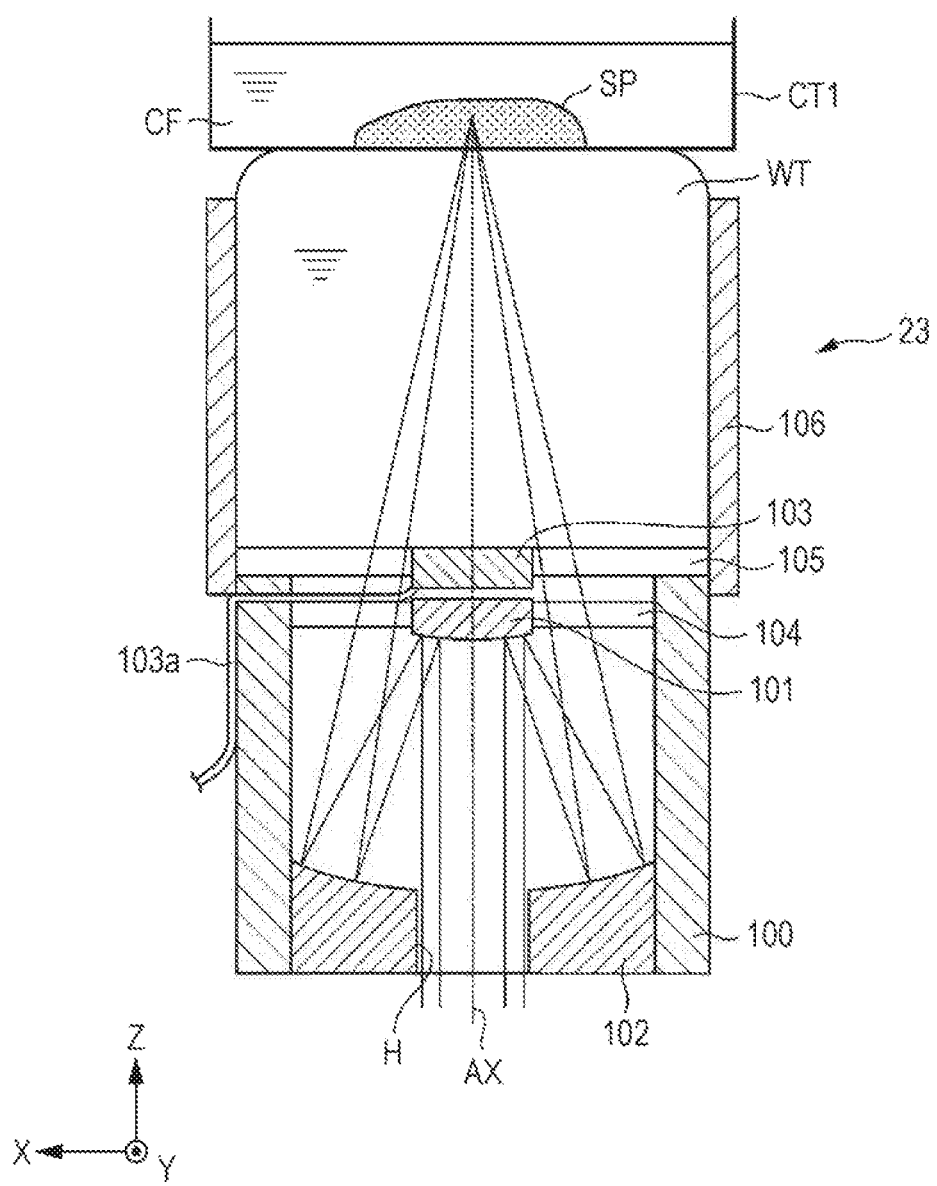
FIG. 2 is a cross-sectional view showing a main configuration of an objective optical system according to the first embodiment of the present invention.

FIG. 2 is a cross-sectional view showing a main configuration of the objective optical system according to the first embodiment of the present invention. As shown in FIG. 2, the objective optical system 23 of the present embodiment includes a lens barrel 100, a convex mirror 101 (first mirror), a concave mirror 102 (second mirror), an ultrasonic detector 103 (detector), a mirror holding member 104, a glass cover 105 (cover member), and a water receiving member 106 (liquid holding member). The lens barrel 100 is a circular annular member for holding the convex mirror 101 and the concave mirror 102 therein. Note that a shape of the lens barrel 100 is not limited to a circular annular shape, but may be another shape (for example, a square annular shape).

The convex mirror 101 is disposed on the optical axis AX of the pulsed light traveling toward the sample SP, and is a mirror having a convex reflecting surface for reflecting the pulsed light traveling toward the sample SP. Specifically, the convex mirror 101 is held by the mirror holding member 104 so that its central portion is disposed on the optical axis AX on one end side (the +Z side) of the lens barrel 100. A position of the convex mirror 101 is a pupil position of the objective optical system 23. The convex mirror 101 is optically conjugated with inside or vicinity of the scanning optical unit 13 by the imaging lens 21 provided in the inverted microscope 20, the pupil projection lens 14 provided in the confocal unit 10, and the like.

Figure 3:
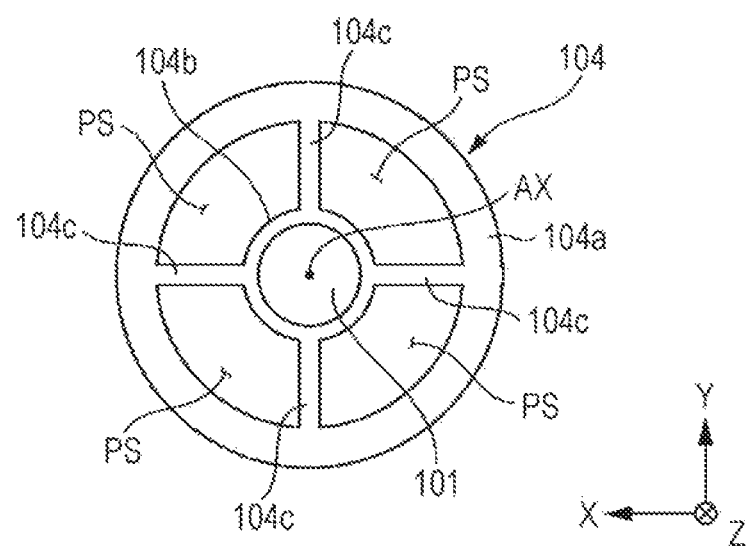
FIG. 3 is a bottom view showing a mirror holding member in the first embodiment of the present invention.

FIG. 3 is a bottom view showing the mirror holding member in the first embodiment of the present invention. As shown in FIG. 3, the mirror holding member 104 has two circular annular portions 104a and 104b having different concentric diameters, and is configured such that the circular annular portions 104a and 104b are connected by a plurality of (four in an example shown in FIG. 3) connecting members 104c extending radially. The circular annular portion 104a has an outer diameter substantially the same as an inner diameter of the lens barrel 100, and is a portion that is fixed to an inner wall of the lens barrel 100. The circular annular portion 104b has an inner diameter substantially the same as an outer diameter of the convex mirror 101, and is a portion in which the convex mirror 101 is fixed. Since the circular annular portion 104a and the circular annular portion 104b are connected by the connecting members 104c, the convex mirror 101 is supported inside the lens barrel 100. A space (excluding the connecting members 104c) between the circular annular portion 104a and the circular annular portion 104b is a passage portion PS through which the pulsed light (pulsed light reflected by the concave mirror 102) passes.

The concave mirror 102 is a mirror having a concave reflecting surface for reflecting the pulsed light reflected by the convex mirror 101 and irradiating the sample SP with the light. The reflecting surface of the concave mirror 102 is designed so that the reflected pulsed light is focused on the sample SP. The concave mirror 102 has an outer diameter substantially the same as the inner diameter of the lens barrel 100, and a hole portion H through which the pulsed light traveling toward the sample SP (the pulsed light reflected in the +Z direction by the mirror 22) passes is formed in its central portion. The concave mirror 102 is held on the other end side (the −Z side) of the lens barrel 100 so that the hole portion H is disposed on the optical axis AX.

The ultrasonic detector 103 is provided on the +Z side (an object side) of the convex mirror 101 in a state where its one end portion provided with a detection surface faces the sample SP side (+Z side), and detects the acoustic wave obtained by irradiating the sample SP with the pulsed light. Specifically, the ultrasonic detector 103 is attached to a central portion of the glass cover 105 that is a glass disk-shaped member, and the glass cover 105 is attached to the lens barrel 100 so as to close the one end side (+Z side: object side end portion) of the lens barrel 100, so that the ultrasonic detector 103 is disposed on the +Z side of the convex mirror 101. Thus, the ultrasonic detector 103 is supported by the glass cover 105 on the +Z side of the convex mirror 101, and is disposed outside an optical path of the pulsed light irradiated to the sample SP so as not to block the light irradiated to the sample SP.

Figure 4:
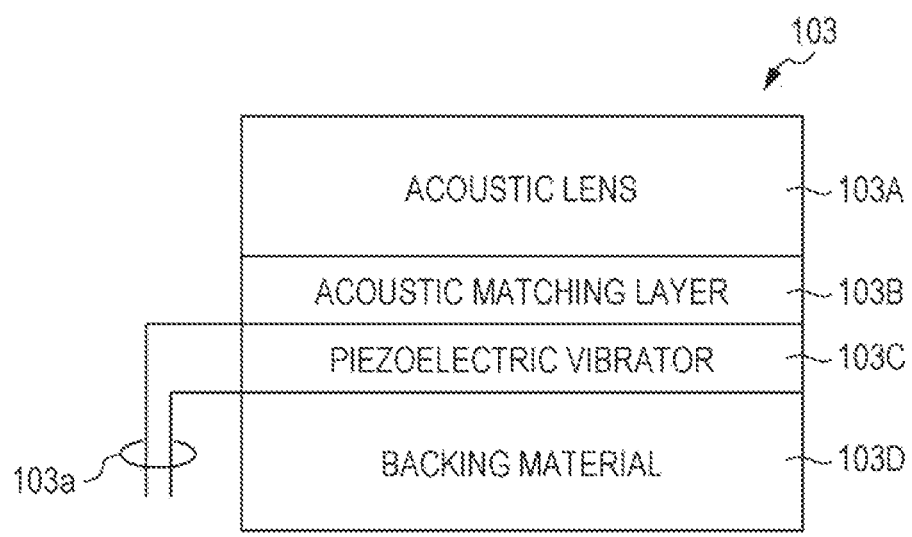
FIG. 4 is a cross-sectional view schematically showing a configuration of an ultrasonic detector in the first embodiment of the present invention.

FIG. 4 is a cross-sectional view schematically showing a main configuration of the ultrasonic detector according to the first embodiment of the present invention. As shown in FIG. 4, the ultrasonic detector 103 includes an acoustic lens 103A, an acoustic matching layer 103B, a piezoelectric vibrator 103C, and a backing material 103D. The ultrasonic detector 103 is supported by the glass cover 105 by being coupled to the glass cover 105 in a state where the acoustic lens 103A is disposed on the object side (sample SP side).

The acoustic lens 103A collects the acoustic wave obtained by irradiating the sample SP with the pulsed light. Specifically, the acoustic lens 103A has a focal position that matches a focal position of the pulsed light, and selectively collects the acoustic wave generated at and near the focal position of the pulsed light. The acoustic matching layer 103B is a layer for matching acoustic impedance, and the acoustic lens 103A is bonded to one surface thereof, and the piezoelectric vibrator 103C is bonded to the other surface thereof.

The piezoelectric vibrator 103C is an element that detects the acoustic wave through the acoustic lens 103A and the acoustic matching layer 103B and outputs the detection signal. Electrodes (not shown) are provided on both surfaces of the piezoelectric vibrator 103C, and lines 103a are respectively electrically connected to the electrodes. The detection signal of the piezoelectric vibrator 103C is output from the lines 103a. The backing material 103D suppresses excessive vibration of the piezoelectric vibrator 103C and is bonded to a back surface (a surface opposite to a surface to which the acoustic matching layer 103B is bonded) of the piezoelectric vibrator 103C.

Here, as shown in FIG. 2, the convex mirror 101, the concave mirror 102, and the ultrasonic detector 103 are arranged in an order of the concave mirror 102, the convex mirror 101, and the ultrasonic detector 103, in the direction from the −Z side to the +Z side on the optical axis AX of the pulsed light traveling toward the sample SP. The detection signal of the ultrasonic detector 103 is output to the controller 30 through the lines 103a. The lines 103a of the ultrasonic detector 103 are drawn to the +Z side of the connecting members 104c forming the mirror holding member 104, and extended from a side surface of the lens barrel 100 to the outside. This is done so as not to block the pulsed light passing through the passage portion PS shown in FIG. 3 as much as possible.

The water receiving member 106 is provided on the one end side (+Z side: object side end portion) of the lens barrel 100 so that its one end portion (−Z side end portion) surrounds a periphery of the glass cover 105, and is a tubular member that can hold a liquid WT therein. As shown in FIG. 2, a bottom portion of the sample container CT1 is disposed close to the other end portion (+Z side end portion) of the water receiving member 106. A space between the glass cover 105 disposed at the one end portion of the water receiving member 106 and the bottom portion of the sample container CT1 disposed in the vicinity of the other end portion of the water receiving member 106 is filled with the liquid WT held in the water receiving member 106.

This is in order that the acoustic wave obtained from the sample SP is detected by the ultrasonic detector 103 without being attenuated as much as possible. That is, since a path through which the acoustic wave is transmitted from the sample SP to the ultrasonic detector 103 is filled with the liquid (culture fluid CF in the sample container CT1 and liquid WT), it is possible to detect the acoustic wave obtained from the sample SP by the ultrasonic detector 103 without being attenuated as much as possible. As described above, since the objective optical system 23 is configured to be movable in the Z direction, a distance between the other end (+Z side end portion) of the water receiving member 106 and the bottom portion of the sample container CT1 may be changed. However, as schematically shown also in FIG. 2, it is possible to maintain the above-described state (the state where the space between the glass cover 105 and the bottom portion of the sample container CT1 is filled with the liquid WT) by surface tension of the liquid WT.

<Operation of Photoacoustic Imaging Apparatus>

(1) Operation when Generating Fluorescence Image

When the operation of the photoacoustic imaging apparatus 1 is started, the laser light source 11 is first controlled by the controller 30, and the pulsed light is emitted in the −Z direction from the laser light source 11. The pulsed light emitted from the laser light source 11 is reflected in the +X direction by the dichroic mirror 12 and then incident on the inverted microscope 20 through the scanning optical unit 13 and the pupil projection lens 14 in this order. The pulsed light incident on the inverted microscope 20 passes through the imaging lens 21 and is then reflected in the +Z direction by the mirror 22 to be incident on the objective optical system 23.

The pulsed light incident on the objective optical system 23 passes through the hole portion H formed in the concave mirror 102 and is incident on and reflected by the convex mirror 101, and then incident on and reflected by the concave mirror 102 to be irradiated to the sample SP. At this time, the pulsed light is irradiated so as to be focused on the sample SP. When the pulsed light is irradiated to the sample SP, the fluorescence is emitted from fluorescent substance contained in the sample SP.

The fluorescence emitted from the sample SP travels in a reverse direction along the optical path of the pulsed light, and is guided to the dichroic mirror 12 through the objective optical system 23, the mirror 22, the imaging lens 21, the pupil projection lens 14, and the scanning optical unit 13 in this order. The fluorescence guided to the dichroic mirror 12 transmits through the dichroic mirror 12 and is then incident on the fluorescence filter 15. Only a specific wavelength component transmits through the fluorescence filter 15 out of wavelength components included in the fluorescence. The wavelength component transmitted through the fluorescence filter 15 is incident on the pinhole 17 through the lens 16, and only the light from a focal plane transmits through the pinhole 17 to be incident on and detected by the photodetector 18.

The detection signal of the photodetector 18 is output to the controller 30 and converted into a digital signal, to be associated with a scanning position (scanning position in an XY plane by the scanning optical unit 13 and the scanning position in the Z direction by the objective optical system 23). The above operation is performed while changing the scanning position in the XY plane by the scanning optical unit 13 (and further changing the scanning position in the Z direction by the objective optical system 23).

Here, as described above, since the pupil position of the objective optical system 23 (the position of the convex mirror 101) is optically conjugated with the inside of the scanning optical unit 13 provided in the confocal unit 10 or the vicinity thereof, even when the pulsed light to be irradiated to the sample SP is scanned by the scanning light unit 13, almost all the pulsed light passes through the pupil position of the objective optical system 23. That is, a state equivalent to scanning the pulsed light at the pupil position of the objective optical system 23 is obtained. Thus, loss of the pulsed light can be reduced. A two-dimensional or three-dimensional fluorescence image is generated by performing such an operation. The generated fluorescence image may be displayed on the display monitor 31 or stored in an internal memory (not shown).

(2) Operation when Generating Photoacoustic Image

When the operation of the photoacoustic imaging apparatus 1 is started, the pulsed light is emitted from the laser light source 11 and irradiated to the sample SP through the above-described optical path, as when generating the fluorescence image. Here, when there is a substance that absorbs the irradiated pulsed light inside the sample SP, the sample SP is locally heated and rapidly expands, so that a local acoustic wave is emitted from the sample SP. The acoustic wave passes through the sample container CT1 and then travels through the liquid WT held inside the water receiving member 106 to be detected by the ultrasonic detector 103.

In consideration of transmission of the acoustic wave, the sample container CT1 is preferably formed of a material whose acoustic impedance density is close to the acoustic impedance density of the liquid WT. For example, when the sample container CT1 is formed of a resin such as polystyrene, the acoustic impedance is closer to the acoustic impedance of the liquid WT than when the sample container CT1 is formed of glass. This is preferable because loss of ultrasonic transmission is reduced.

At this time, in the ultrasonic detector 103, the acoustic wave generated near a focal point of the pulsed light is selectively collected by the acoustic lens 103A shown in FIG. 4, and the acoustic wave is efficiently transmitted to the piezoelectric vibrator 103C without being almost not reflected by the acoustic matching layer 103B and converted into an electric signal (the detection signal). Extra vibration of the piezoelectric vibrator 103C is suppressed by the backing material 103D bonded to the piezoelectric vibrator 103C. Therefore, the piezoelectric vibrator 103C outputs the detection signal having a high signal level and low noise.

The detection signal of the ultrasonic detector 103 is output to the controller 30 and converted into the digital signal, to be associated with the scanning position (the scanning position in the XY plane by the scanning optical unit 13 and the scanning position in the Z direction by the objective optical system 23). The above operation is performed while changing the scanning position in the XY plane by the scanning optical unit 13 (and further changing the scanning position in the Z direction by the objective optical system 23).

Here, since the pupil position of the objective optical system 23 (the position of the convex mirror 101) is optically conjugated with the inside of the scanning optical unit 13 provided in the confocal unit 10 or the vicinity thereof, even when the pulsed light to be irradiated to the sample SP with the scanning optical unit 13 is scanned by the scanning light unit 13, almost all the pulsed light passes through the pupil position of the objective optical system 23. That is, the state equivalent to scanning the pulsed light at the pupil position of the objective optical system 23 is obtained. Thus, the loss of the pulsed light can be reduced even when generating the photoacoustic image. A two-dimensional or three-dimensional photoacoustic image is generated by performing such an operation. The generated photoacoustic image may be displayed on the display monitor 31 or stored in the internal memory (not shown).

As described above, the present embodiment uses the objective optical system 23 including the convex mirror 101 that reflects the pulsed light traveling toward the sample SP, the concave mirror 102 that reflects the pulsed light reflected by the convex mirror 101 and irradiates the sample SP with the light, and the ultrasonic detector 103 that is provided on the object side of the convex mirror 101 and detects the acoustic wave obtained by irradiating the sample SP with the light. Thus, unlike the related art, there is no need to arrange a separating member for separating the light pulse and the acoustic signal on the object side of the objective lens, and the objective optical system 23 can be disposed closer to the sample SP than before. Therefore, since it is possible to prevent attenuation and aberration of the acoustic wave, and to use the objective optical system 23 having a large numerical aperture (for example, the objective optical system 23 having a numerical aperture of about 0.3 to 0.5), it is possible to obtain a clear image with higher resolution than before.

In the present embodiment, since the ultrasonic detector 103 is disposed on the object side of the convex mirror 101, it is possible to reduce the pulsed light blocked by the ultrasonic detector 103 as much as possible out of the pulsed light that is reflected by the concave mirror 102 and irradiated to the sample SP. In addition, since the pulsed light irradiated to the ultrasonic detector 103 can be reduced as much as possible, it is possible to reduce noise due to thermal expansion generated when the pulsed light is irradiated to the ultrasonic detector 103.

Since the objective optical system 23 is a reflective optical system including the convex mirror 101 and the concave mirror 102, the aberration does not occur over a wide wavelength band from ultraviolet to infrared. Thus, it is possible to observe the sample SP using the pulsed light of various wavelengths. In addition, since the objective optical system 23, which is the reflective optical system, has a small dispersion, a pulse width of short pulse light can be maintained. Further, since the optical path (route) from the sample SP to the ultrasonic detector 103 is filled with the liquid WT, it is possible to improve both transmittivity of the pulsed light and transmittivity of the acoustic wave.

In the present embodiment, the pupil position of the objective optical system 23 (the position of the convex mirror 101) is optically conjugated with the inside of the scanning optical unit 13 provided in the confocal unit 10 or the vicinity thereof. Thus, even when the pulsed light to be irradiated to the sample SP is scanned by the scanning light unit 13, almost all the pulsed light passes through the pupil position of the objective optical system 23. Therefore, in the present embodiment, the loss of the pulsed light can be reduced and light utilization efficiency can be improved.

In the above-described embodiment, in order to facilitate understanding, the operation when generating the fluorescence image and the operation when generating the photoacoustic image have been described separately. However, when the sample SP is irradiated with the pulsed light emitted from the laser light source 11, the fluorescence is emitted from the fluorescent substance contained in the sample SP, and at the same time, the local acoustic wave is emitted from the sample SP. Therefore, the controller 30 can also simultaneously generate the fluorescence image and the photoacoustic image based on a detection result of the ultrasonic detector 103 provided in the objective optical system 23 and a detection result of the photodetector 18 provided in the confocal unit 10. Thus, it is possible to superimpose the fluorescence image and the photoacoustic image of the same observation place obtained by performing observation simultaneously. Further, in the present embodiment, since the sample SP is observed by immersion, the resolution can be improved as compared with the case of observing the sample SP without immersion.

Second Embodiment

<Photoacoustic Imaging Apparatus>

Figure 5:
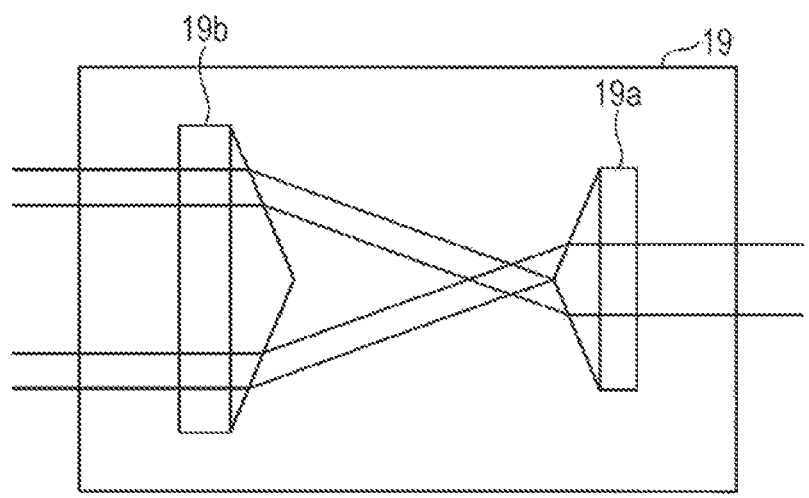
FIG. 5 is a diagram showing a configuration of an optical system provided in the photoacoustic imaging apparatus according to a second embodiment of the present invention.
Figure 6:
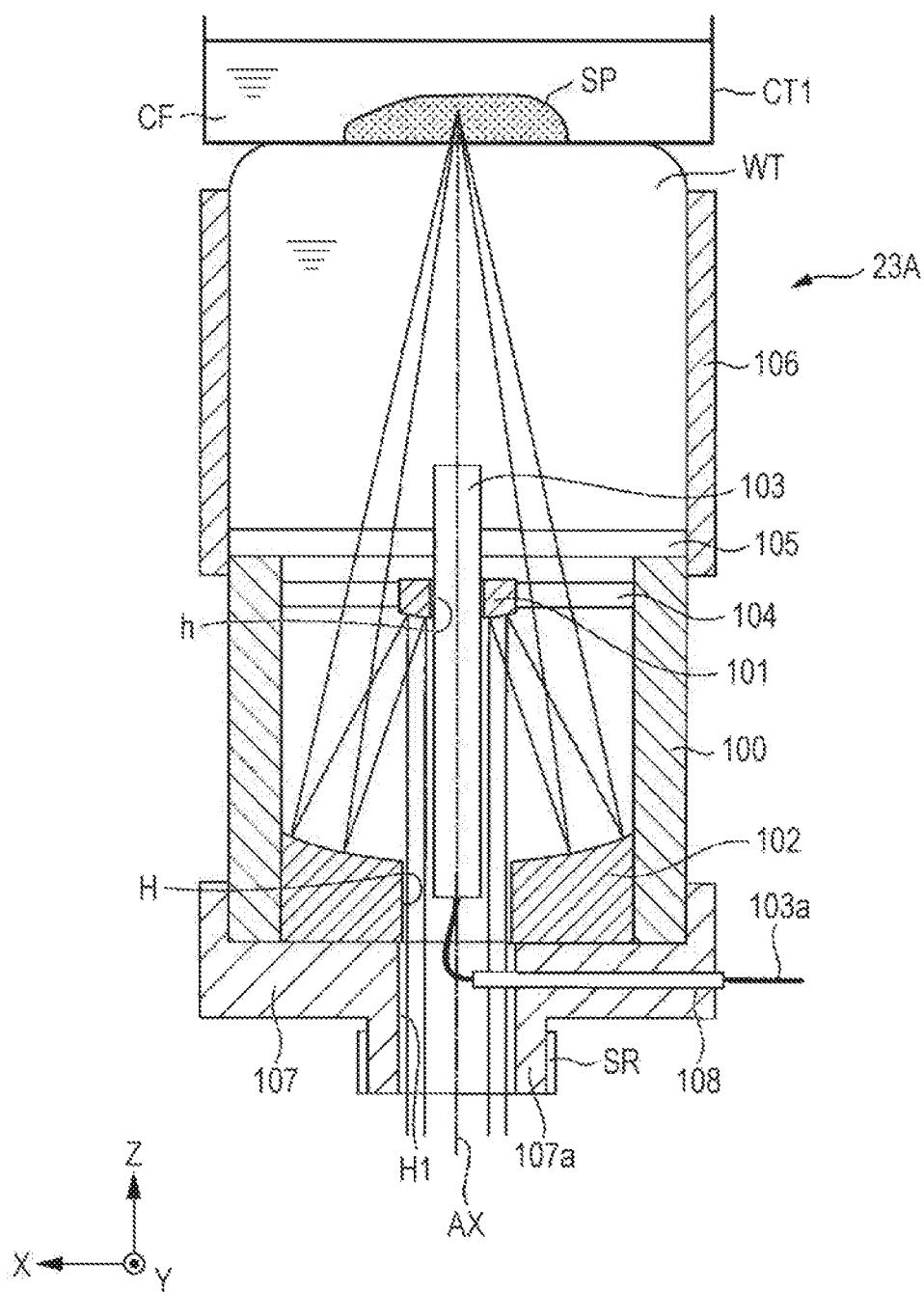
FIG. 6 is a cross-sectional view showing the main configuration of the objective optical system according to the second embodiment of the present invention.

An overall configuration of the photoacoustic imaging apparatus of the present embodiment is a configuration in which an optical system 19 shown in FIG. 5 is added to the photoacoustic imaging apparatus 1 shown in FIG. 1, and the objective optical system 23 is replaced with an objective optical system 23A shown in FIG. 6. FIG. 5 is a diagram showing a configuration of an optical system provided in the photoacoustic imaging apparatus according to a second embodiment of the present invention. As shown in FIG. 5, the optical system 19 includes two axicon lenses 19a and 19b arranged so that their apex angles are opposed to each other, and is an optical system for converting a cross-sectional shape (shape in a plane perpendicular to the optical axis) of incident light. Specifically, the optical system 19 shown in FIG. 5 converts light having a circular cross-sectional shape that travels from the right side of the drawing to the left side of the drawing into light having a ring-shaped cross-section. On the contrary, the light having a ring-shaped cross-section that travels from the left side to the right side of the drawing is converted into the light having a circular cross-sectional shape.

Such an optical system 19 is desirably arranged, for example, on the optical path between the imaging lens 21 and the mirror 22 provided in the inverted microscope 20 shown in FIG. 1, or on the optical path from the laser light source 11 to the scanning optical unit 13 provided in the confocal unit 10. With this arrangement, the cross-sectional shape of the light incident on the objective optical system 23A (light incident on the convex mirror 101) shown in FIG. 6 can be made ring-shaped.

Thus, the light incident on the central portion of the convex mirror 101 that does not contribute to measurement can be eliminated, so that the light utilization efficiency can be improved. In addition, since reflected light in the central portion of the convex mirror 101 can be eliminated, so that the noise can be reduced. The operation of the photoacoustic imaging apparatus of the present embodiment is the same as the operation of the photoacoustic imaging apparatus 1 shown in FIG. 1 except that the light (light having a ring-shaped cross-section) converted by the optical system 19 is incident on the objective optical system 23A. Therefore, detailed description of the operation of the photoacoustic imaging apparatus of the present embodiment will be omitted.

<Objective Optical System>

FIG. 6 is a cross-sectional view showing the main configuration of the objective optical system according to the second embodiment of the present invention. In FIG. 6, members corresponding to those shown in FIG. 2 are denoted by the same reference numerals. As shown in FIG. 6, the objective optical system 23A of the present embodiment has a configuration in which a rod-shaped ultrasonic detector 103 is used, and a rear end cover 107 and a wiring protection tube 108 are added thereto accordingly.

The ultrasonic detector 103 is a rod-shaped device in which the acoustic lens 103A, the acoustic matching layer 103B, the piezoelectric vibrator 103C, and the backing material 103D illustrated in FIG. 4 are housed in, for example, a cylindrical metal casing. The ultrasonic detector 103 is disposed so that its longitudinal direction is in the Z direction, and is water-tightly bonded to the glass cover 105 with its one end portion being disposed closer to the object side (+Z side) from the glass cover 105. Here, the ultrasonic detector 103 is attached to the glass cover 105 so that the focal position of the acoustic lens 103A provided therein coincides with the focal position of the objective optical system 23A (the focal position of the pulsed light). The convex mirror 101 is the same mirror as the convex mirror 101 shown in FIG. 2, however, a hole portion h in which the ultrasonic detector 103 is to be inserted is formed in the central portion thereof.

The rear end cover 107 is, for example, a substantially bottomed circular annular member, and is attached to the other end side (−Z side) of the lens barrel 100. A hole portion H1 through which the pulsed light traveling toward the sample SP (pulsed light reflected in the +Z direction by the mirror 22) passes is formed in a central portion of the rear end cover 107. Further, a bottom surface of the rear end cover 107 is provided with a projecting portion 107a that has the same inner diameter as the hole portion H1 and projects in the −Z direction with a threaded portion SR formed on its outer surface. The objective optical system 23A is fixed to the inverted microscope 20 by screwing the threaded portion SR of the projecting portion 107a to a support member (not shown). The inner diameter of the hole portion H1 formed in the rear end cover 107 is substantially the same as that of the hole portion H formed in the central portion of the concave mirror 102. Note that the light incident on the objective optical system 23A is the light having a ring-shaped cross-section converted by the optical system 19 shown in FIG. 5. Therefore, although the ultrasonic detector 103 is disposed on the optical axis AX, it is disposed outside the optical path (inside the ring) of the pulsed light irradiated to the sample SP so as not to block the light irradiated to the sample SP.

The wiring protection tube 108 is a pipe for protecting the line 103a extending from the other end portion of the ultrasonic detector 103. For example, a hollow circular annular metal pipe can be used as the wiring protection tube 108. The wiring protection tube 108 is provided in the rear end cover 107 so that one end thereof is disposed at the central portion of the hole portion H1 formed in the rear end cover 107 (the portion close to the optical axis AX not irradiated with light), and the other end thereof is disposed on one surface side of the rear end cover 107. The line 103a extending from the other end portion of the ultrasonic detector 103 is inserted into the wiring protection tube 108 from one end of the wiring protection tube 108, and drawn out from the other end of the wiring protection tube 108 to the outside of the wiring protection tube 108 (the outside of objective optical system 23A).

The objective optical system 23A having such a configuration uses the rod-shaped ultrasonic detector 103 that is more general than the ultrasonic detector used in the first embodiment, so that the same effects as in the first embodiment can be obtained. Further, in the objective optical system 23A having such a configuration, the light incident on the objective optical system 23A (light having a ring-shaped cross-section) is irradiated to the wiring protection tube 108, however, since the light is not irradiated to the line 103a inserted into the wiring protection tube 108, the wiring 103a can be protected.

<Modification of Objective Optical System>

Figure 7:
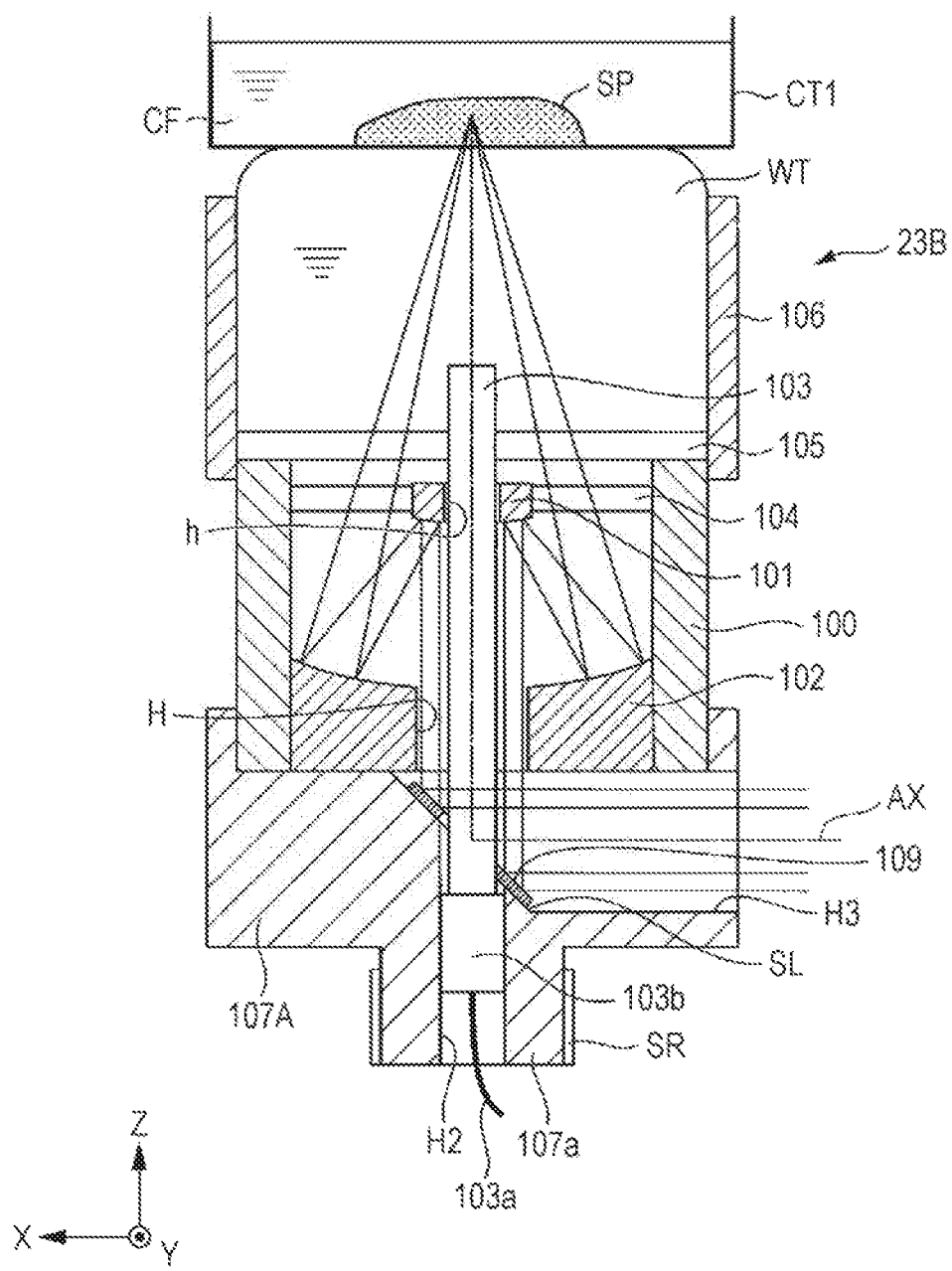
FIG. 7 is a cross-sectional view showing a modification of the objective optical system according to the second embodiment of the present invention.

FIG. 7 is a cross-sectional view showing a modification of the objective optical system according to the second embodiment of the present invention. In FIG. 7, the members corresponding to those shown in FIG. 6 are denoted by the same reference numerals. As shown in FIG. 7, the objective optical system 23B of the present embodiment has a configuration in which the rod-shaped ultrasonic detector 103 is used in the same manner as the objective optical system 23A shown in FIG. 6, and a rear end cover 107A and a circular annular mirror 109 are added thereto accordingly. Further, the objective optical system 23B of the present embodiment is configured such that the light having a ring-shaped cross-section is incident from the side (from the −X side). Such an objective optical system 23B is used, for example, by omitting the mirror 22 shown in FIG. 1 and being placed at a position where the omitted mirror 22 was placed.

The ultrasonic detector 103 is the same as that shown in FIG. 6, but a holding portion 103b is provided at the other end portion thereof. The holding portion 103b is a portion fixed to the rear end cover 107A, and has an outer diameter larger than that of a main body portion of the ultrasonic detector 103. The ultrasonic detector 103 is disposed so that its longitudinal direction is in the Z direction, and is water-tightly bonded to the glass cover 105 with the one end portion being disposed closer to the object side (+Z side) from the glass cover 105, in the same manner as that shown in FIG. 6. The ultrasonic detector 103 is attached to the glass cover 105 so that the focal position of the acoustic lens 103A provided therein coincides with the focal position of the objective optical system 23B (the focal position of the pulsed light).

The rear end cover 107A is, for example, the substantially bottomed circular annular member, and is attached to the other end side (−Z side) of the lens barrel 100. A hole portion H2 extending in the Z direction is formed in the central portion of the rear end cover 107A, and a hole portion H3 extending in the X direction is formed on one side surface of the rear end cover 107A. A holding portion 103b of the ultrasonic detector 103 is inserted into the hole portion H2, and the pulsed light having a ring-shaped cross-section (the pulsed light traveling in the +X direction through the imaging lens 21) is incident on the hole portion H3. A bottom surface (surface on the +X side) of the hole portion H3 is a slope SL having an angle of 45° with the XY plane.

Further, the bottom surface of the rear end cover 107A is provided with the projecting portion 107a that has the same inner diameter as the hole portion H2 and projects in the −Z direction with the threaded portion SR formed on the outer surface. The objective optical system 23B is fixed to the inverted microscope 20 by screwing the threaded portion SR of the projecting portion 107a to the support member (not shown). The inner diameter of the hole portion H2 formed in the rear end cover 107A is smaller than the hole portion H formed in the central portion of the concave mirror 102, and is approximately equal to the outer diameter of the holding portion 103b of the ultrasonic detector 103. The inner diameter of the hole portion H3 formed in the rear end cover 107A is, for example, approximately equal to the diameter of the hole portion H formed in the central portion of the concave mirror 102.

The circular annular mirror 109 is a circular annular flat mirror, and is disposed on the slope SL formed on the rear end cover 107A. That is, the circular annular mirror 109 is disposed at an angle of 45° with respect to the XY plane. The circular annular mirror 109 is provided to reflect the pulsed light incident on the hole portion H3 of the rear end cover 107A in the +Z direction. That is, the circular annular mirror 109 is provided to bend the optical axis AX of the pulsed light incident on the hole portion H3 of the rear end cover 107A by 90°. As shown in FIG. 7, the ultrasonic detector 103 is inserted into the circular annular mirror 109. In the present embodiment, the line 103a is drawn to the outside (outside of the objective optical system 23B) through the hole portion H2 formed in the rear end cover 107A.

The objective optical system 23B having such a configuration can obtain the same effects as the first embodiment by using a general rod-shaped ultrasonic detector 103 in the same manner as the objective optical system 23A shown in FIG. 6. In the objective optical system 23B having such a configuration, the ultrasonic detector 103 can be firmly supported by the glass cover 105 and the rear end cover 107. Further, in the objective optical system 23B having such a configuration, a member (the wiring protection tube 108 shown in FIG. 6) for protecting the line 103a can be omitted.

Third Embodiment

<Photoacoustic Imaging Apparatus>

Figure 8:
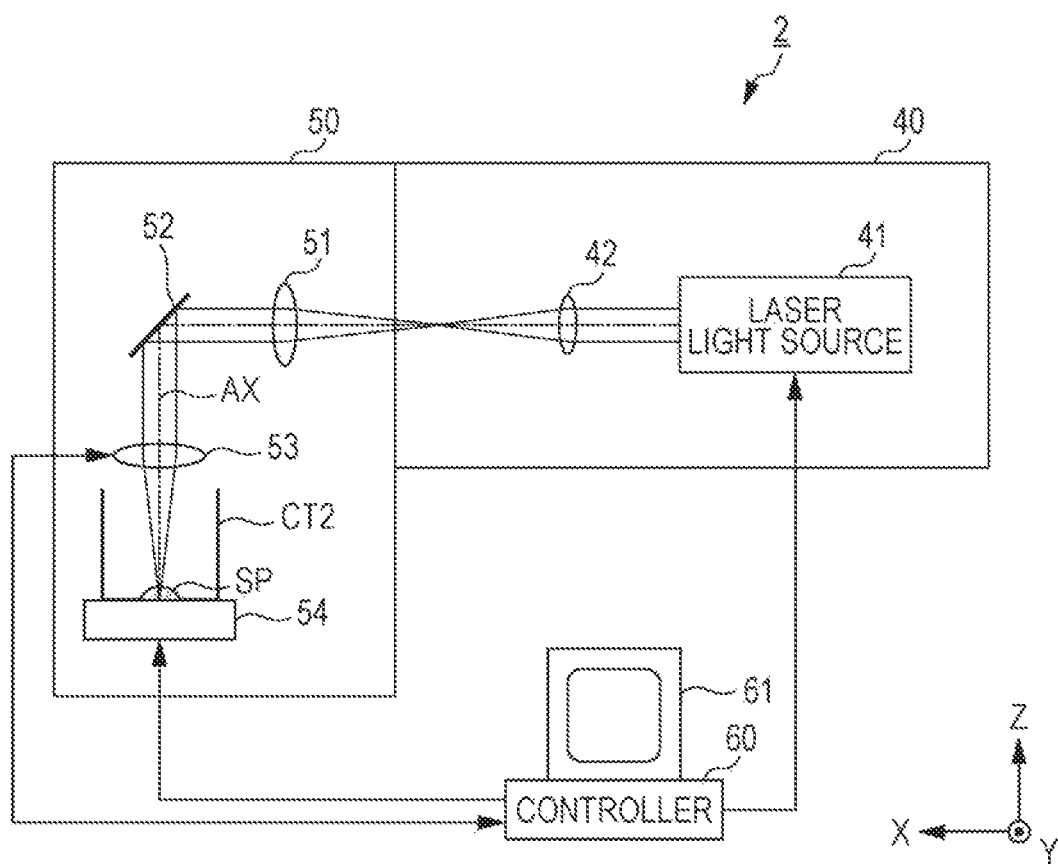
FIG. 8 is a diagram showing the main configuration of the photoacoustic imaging apparatus according to a third embodiment of the present invention.

FIG. 8 is a diagram showing the main configuration of the photoacoustic imaging apparatus according to a third embodiment of the present invention. As shown in FIG. 8, a photoacoustic imaging apparatus 2 of the present embodiment includes a confocal unit 40, an upright microscope 50, and a controller 60, and generates the photoacoustic image of the sample SP based on the acoustic wave obtained by irradiating the sample SP stored in a sample container CT2 with the pulsed light. Although the photoacoustic imaging apparatus 1 of the first embodiment can generate the fluorescence image and the photoacoustic image, the photoacoustic imaging apparatus 2 of the present embodiment can generate only the photoacoustic image of the sample SP.

The confocal unit 40 is a unit forming a main portion of the confocal microscope, and the confocal microscope is realized by attaching the upright microscope 50 to the confocal unit 40. Note that not only the upright microscope 50 can be attached to the confocal unit 40, but other microscopes (for example, the inverted microscope) can also be attached thereto. That is, an arbitrary microscope can be attached to the confocal unit 40 according to the application of the confocal microscope in the same manner as the confocal unit 10 of the first embodiment.

The confocal unit 40 includes a laser light source 41 and a matching lens 42. The laser light source 41 emits the pulsed light for irradiating the sample SP stored in the sample container CT2 under the control of the controller 60. As in the first embodiment, the wavelength of the pulsed light emitted from the laser light source 41 can be any wavelength depending on the sample SP, and the laser light source 41 may be capable of changing the wavelength continuously or discretely. The matching lens 42 is disposed on the +X side of the laser light source 41 and is a lens for matching the pulsed light emitted from the laser light source 41 with the upright microscope 50.

The upright microscope 50 includes an imaging lens 51, a mirror 52, an objective optical system 53, and a moving stage 54, and observes the sample SP stored in the sample container CT2 from the upper side (+Z side). The imaging lens 51 is a lens for converting the pulsed light emitted from the confocal unit 40 and incident on the upright microscope 50 into the parallel light. The mirror 52 is disposed in the +X direction of the imaging lens 51, and reflects the pulsed light traveling in the +X direction in the −Z direction through the imaging lens 51.

The objective optical system 53 is disposed on the −Z side of the mirror 52, collects the pulsed light reflected in the −Z direction by the mirror 52 and irradiates the sample SP with the light, and detects the acoustic wave obtained by irradiating the sample SP with the pulsed light. The detection signal from the objective optical system 53 is output to the controller 30. The objective optical system 53 is configured to be movable in the Z direction under the control of the controller 60 similarly to the objective optical system 23 shown in FIG. 1. Details of the objective optical system 53 will be described below.

The moving stage 54 is a stage on which the sample container CT2 storing the sample SP is placed, and the placed sample container CT2 can be moved in the XY plane under the control of the controller 30. As the moving stage 54, for example, a linear XY stage can be used. Note that the sample container CT2 is filled with the culture fluid CF (see FIG. 9), and the sample SP is immersed in the culture fluid CF.

The controller 60 controls the operation of the photoacoustic imaging apparatus 2 in an integrated manner. For example, the laser light source 11 provided in the confocal unit 40 is controlled to emit or stop the pulsed light irradiated to the sample SP. Further, the objective optical system 53 and the moving stage 54 provided in the upright microscope 50 are controlled to scan the sample SP with the pulsed light (X-axis, Y-axis, and Z-axis scanning). Further, the controller 60 performs signal processing of the detection signal output from the objective optical system 53 to generate the photoacoustic image and display it on a display monitor 61. The display monitor 61 is a monitor provided with, for example, the liquid crystal display device similarly to the display monitor 31 shown in FIG. 1.

<Objective Optical System>

Figure 9:
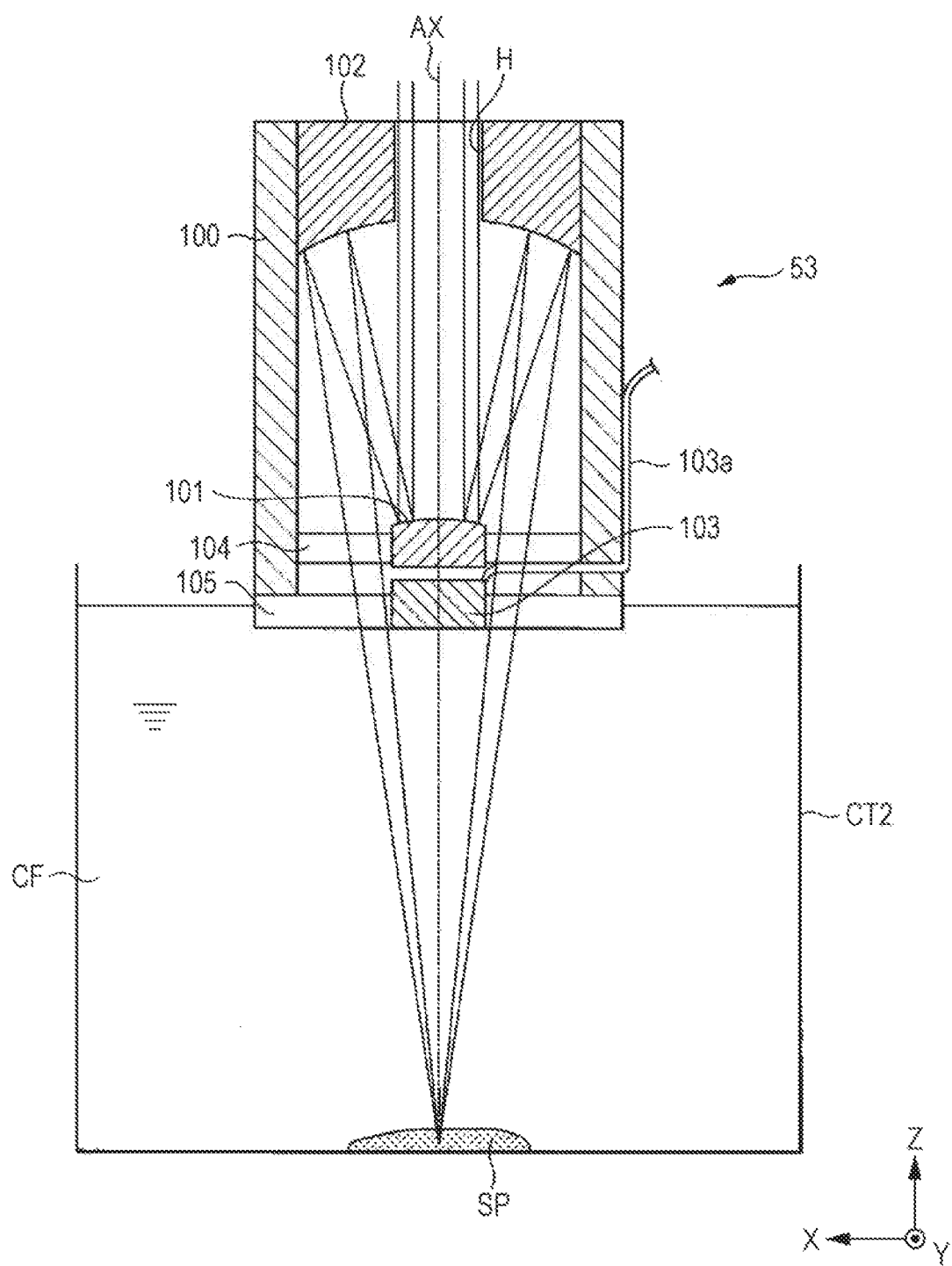
FIG. 9 is a cross-sectional view showing the main configuration of the objective optical system according to the third embodiment of the present invention.

FIG. 9 is a cross-sectional view showing the main configuration of the objective optical system according to the third embodiment of the present invention. In FIG. 9, the members corresponding to those shown in FIG. 2 are denoted by the same reference numerals. As shown in FIG. 9, the objective optical system 53 of the present embodiment is different from the objective optical system 23 shown in FIG. 2 in that the water receiving member 106 is omitted, and the glass cover 105 is in contact with the culture fluid CF in which the sample SP is immersed, with the Z direction being arranged in the opposite direction.

That is, in the objective optical system 53 of the present embodiment, the convex mirror 101, the concave mirror 102, and the ultrasonic detector 103 are arranged in the order of the concave mirror 102, the convex mirror 101, and the ultrasonic detector 103, in the direction from the +Z side to the −Z side on the optical axis AX of the pulsed light traveling toward the sample SP. Further, the objective optical system 53 of the present embodiment is designed to have a smaller numerical aperture (for example, about 0.1) than the objective optical system 23 shown in FIG. 2. This is to obtain a tomographic image (cross-sectional image in the Z direction) of the sample SP at a higher speed than in the first embodiment.

<Operation of Photoacoustic Imaging Apparatus>

When the operation of the photoacoustic imaging apparatus 2 is started, the laser light source 41 is controlled by the controller 60, and the pulsed light is emitted in the +X direction from the laser light source 41. The pulsed light emitted from the laser light source 41 is incident on the upright microscope 50 through the matching lens 42. The pulsed light incident on the upright microscope 50 is converted into the parallel light by the imaging lens 51, and then reflected by the mirror 52 in the −Z direction to be incident on the objective optical system 53.

The pulsed light incident on the objective optical system 53 passes through the hole portion H formed in the concave mirror 102 and is incident on and reflected by the convex mirror 101, and then incident on and reflected by the concave mirror 102 in the same manner as in the first embodiment. Then, the pulsed light reflected by the concave mirror 102 passes through the passage portion PS of the mirror holding member 104, and then sequentially transmits through the glass cover 105 and the culture fluid CF in the sample container CT2 to be irradiated to the sample SP. At this time, the pulsed light is irradiated so as to be focused on the sample SP.

Figure 10:
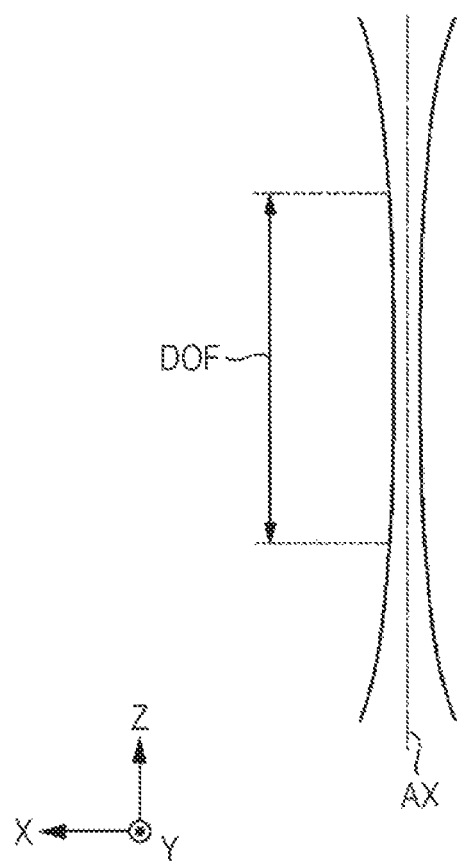
FIG. 10 is an enlarged view of vicinity of a condensing point of pulsed light in the third embodiment of the present invention.

FIG. 10 is an enlarged view of vicinity of a condensing point of the pulsed light in the third embodiment of the present invention. When the objective optical system 53 is designed to have a small numerical aperture (for example, about 0.1) as in the present embodiment, a section in which the condensed diameter of the pulsed light is almost constant is generated as indicated as a depth of focus DOF in FIG. 10. In the present embodiment, the position of the objective optical system 53 in the Z direction is adjusted by the control of the controller 60 so that the position (position in the Z direction) of a deep portion of the sample SP to be observed is within the depth of focus DOF.

When there is a substance that absorbs the irradiated pulsed light inside the sample SP, the sample SP is locally heated and rapidly expands, so that the local acoustic wave is emitted from the sample SP. The acoustic wave is transmitted through the culture fluid CF in the sample container CT2 to be detected by the ultrasonic detector 103. The detection signal of the ultrasonic detector 103 is output to the controller 60, and converted into the digital signal, to be associated with the scanning position (the scanning position in the XY plane by the moving stage 54).

Here, since the controller 60 also controls the laser light source 41 provided in the confocal unit 40, it grasps a time when the pulsed light is emitted from the laser light source 41. The controller 60 can know a depth (position in the Z direction) of acoustic wave generation source by determining how much delayed the detection signal obtained from the ultrasonic detector 103 is obtained after the pulsed light is emitted from the laser light source 41. Thus, it is possible to obtain information on a depth direction (Z-direction information) of the sample SP within the depth of focus DOF by observing the detection signal obtained from the ultrasonic detector 103 in time series after one pulsed light is emitted from the laser light source 41.

The above operation is performed while changing the scanning position in the XY plane by the moving stage 54. By performing such an operation, the photoacoustic image of the tomographic image of the sample SP is generated. Further, when the position of the objective optical system 53 in the Z direction is adjusted by the control of the controller 60, and the same operation is performed while changing the scanning position in the XY plane by the moving stage 54, the photoacoustic image of the tomographic image of the sample SP at a position different in the depth direction (Z direction) is generated. The generated photoacoustic image may be displayed on the display monitor 61 or stored in the internal memory (not shown).

As described above, the present embodiment uses the objective optical system 53 including the convex mirror 101 that reflects the pulsed light traveling toward the sample SP, the concave mirror 102 that reflects the pulsed light reflected by the convex mirror 101 and irradiates the sample SP with the light, and the ultrasonic detector 103 that is provided on the object side of the convex mirror 101 and detects the acoustic wave obtained by irradiating the sample SP with the light. Since the objective optical system 53 has the same configuration as the objective optical system 23 of the first embodiment, it is possible to prevent attenuation and aberration of the acoustic wave. Thus, it is possible to obtain a clearer image than before also in this embodiment.

In the present embodiment, as in the first embodiment, the pulsed light blocked by the ultrasonic detector 103 can be reduced as much as possible, and the noise due to thermal expansion caused when the pulsed light is irradiated to the ultrasonic detector 103 can also be reduced. Further, since the aberration does not occur over the wide wavelength band from ultraviolet to infrared, it is possible to observe the sample SP using the pulsed light of various wavelengths. Furthermore, since the dispersion is small, the pulse width of the short pulse light can be maintained.

In the present embodiment, since the numerical aperture of the objective optical system 53 is designed to be smaller than that of the objective optical system 23 of the first embodiment, the resolution is inferior to that of the first embodiment, however, it is possible to create the tomographic image at a higher speed than in the first embodiment. In the present embodiment, since the upright microscope 50 is used, observation in an upright type is possible, and it is also possible to be used for observation of animals and the like. In the above-described embodiment, although a case where the numerical aperture of the objective optical system 53 is reduced is described as an example, it is possible to increase the numerical aperture of the objective optical system 53 to increase the resolution. Further, in the present embodiment, since the sample SP is observed by immersion, the resolution can be improved as compared with the case of observing the sample SP without immersion.

Fourth Embodiment

<Photoacoustic Imaging Apparatus and Operation>

The overall configuration and operation of the photoacoustic imaging apparatus of the present embodiment are the same as the overall configuration and operation of the photoacoustic imaging apparatus 2 shown in FIG. 8. Therefore, the detailed description of the overall configuration and operation of the photoacoustic imaging apparatus of the present embodiment will be omitted.

<Objective Optical System>

Figure 11:
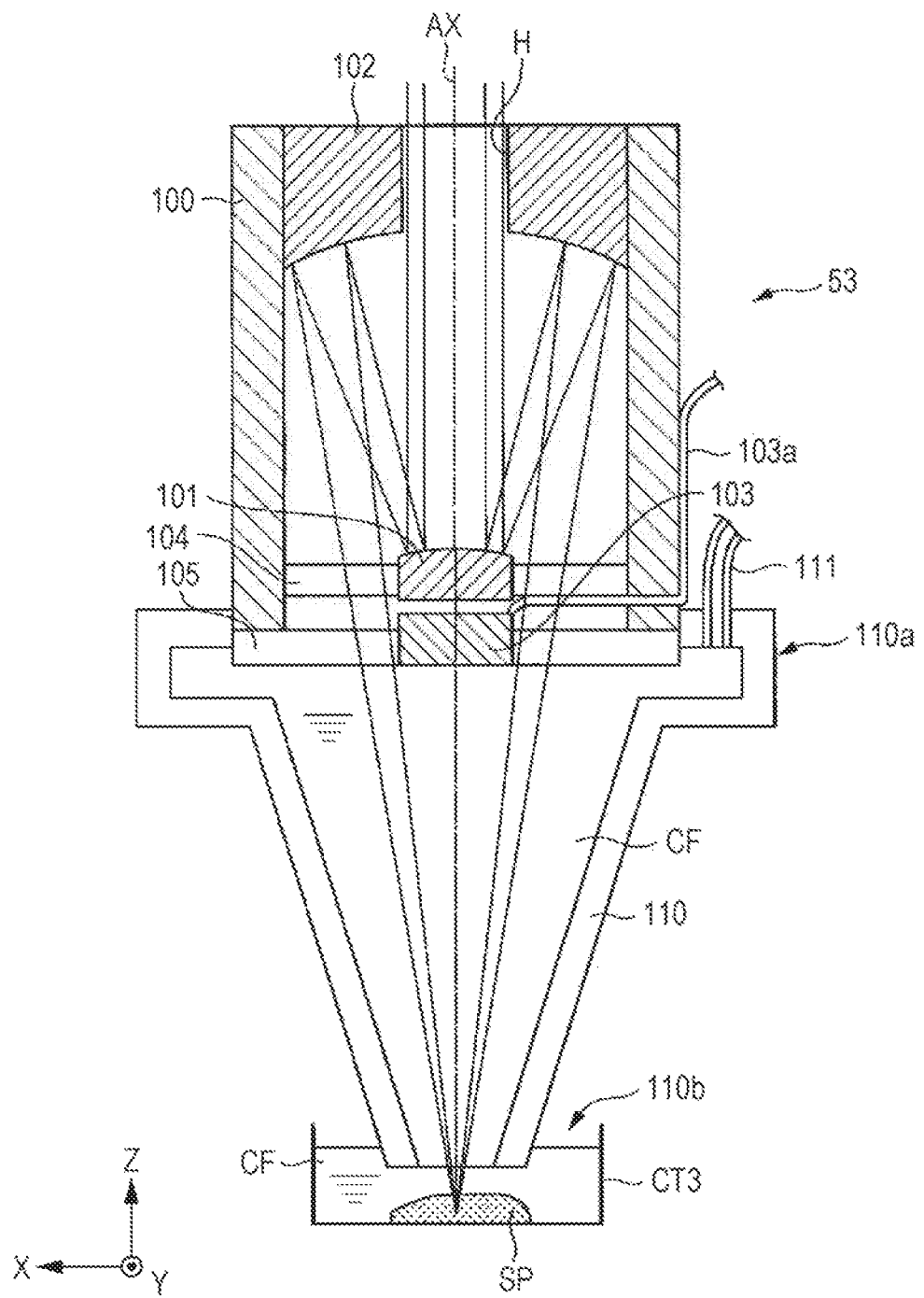
FIG. 11 is a cross-sectional view showing the main configuration of the objective optical system according to a fourth embodiment of the present invention.

FIG. 11 is a cross-sectional view showing the main configuration of the objective optical system according to a fourth embodiment of the present invention. In FIG. 11, the members corresponding to those shown in FIG. 9 are denoted by the same reference numerals. As shown in FIG. 11, the objective optical system 53 of the present embodiment is different from the objective optical system 53 shown in FIG. 9 in that a water receiving member 110 is provided.

The water receiving member 110 is provided on the one end side (−Z side: object side end portion) of the lens barrel 100 so that one end portion 110a surrounds the periphery of the glass cover 105, and is a tubular member having a diameter decreasing from the one end portion 110a to the other end portion 110b. At the one end portion 110a of the water receiving member 110, for example, a suction tube 111 (liquid conduit) connected to a suction pump (not shown) is provided. Further, a diameter of tip of the other end portion 110b of the water receiving member 110 is made smaller than a diameter of the sample container CT3 in which the sample SP is stored.

Therefore, by operating the suction pump (not shown) while the other end portion 110b of the water receiving member 110 is immersed in the culture fluid CF in the sample container CT3, a state in which the culture fluid CF is held inside the water receiving member 110 (a state in which the inside of the water receiving member 110 is filled with the culture fluid CF) can be achieved. In the third embodiment described above, it is necessary to bring the glass cover 105 into contact with the culture fluid CF in the sample container CT2 using the sample container CT2 having a diameter larger than that of the glass cover 105 as shown in FIG. 9, however, in the present embodiment, it is possible to use a sample container CT3 having a smaller diameter than the sample container CT2 used in the third embodiment.

As described above, although the present embodiment is different from the third embodiment in that the water receiving member 110 is provided, the objective optical system 53 having the same configuration as that of the third embodiment is used. Therefore, also in the present embodiment, it is possible to obtain a clearer image than before, and to create the tomographic image at a high speed. In the present embodiment, similarly to the third embodiment, it is possible to reduce the pulsed light blocked by the ultrasonic detector 103 as much as possible, and to reduce the noise due to the thermal expansion caused when the pulsed light is irradiated to the ultrasonic detector 103. Further, it is possible to observe the sample SP using the pulsed light having various wavelengths, and to maintain the pulse width of the short pulse light since the dispersion is small.

Fifth Embodiment

<Photoacoustic Imaging Apparatus>

The overall configuration of the photoacoustic imaging apparatus of the present embodiment is the same as the overall configuration of the photoacoustic imaging apparatus 1 shown in FIG. 1. Therefore, the detailed description of the overall configuration of the photoacoustic imaging apparatus of the present embodiment will be omitted.

<Objective Optical System>

Figure 12:
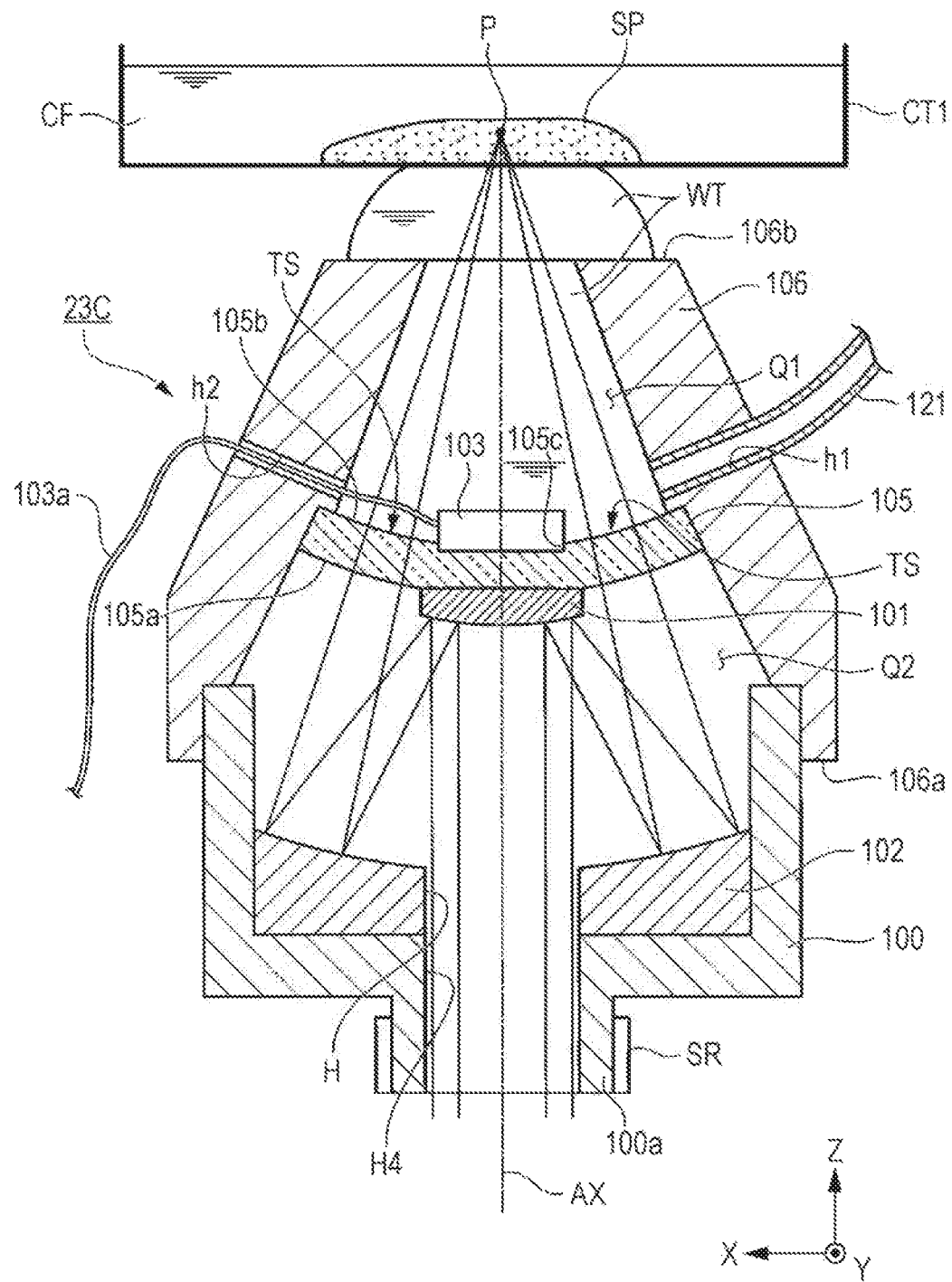
FIG. 12 is a cross-sectional view showing the main configuration of the objective optical system according to a fifth embodiment of the present invention.

FIG. 12 is a cross-sectional view showing the main configuration of the objective optical system according to a fifth embodiment of the present invention. In FIG. 12, the members corresponding to those shown in FIG. 2 are denoted by the same reference numerals. As shown in FIG. 12, an objective optical system 23C of the present embodiment is different from the objective optical system 23 shown in FIG. 2 mainly in that the lens barrel 100, the glass cover 105, and the water receiving member 106 are changed, the mirror holding member 104 is omitted, and a supply tube 121 (liquid conduit) is added.

The lens barrel 100 is the substantially bottomed circular annular member, and holds the concave mirror 102 therein. A hole portion H4 through which the pulsed light traveling toward the sample SP (pulsed light reflected in the +Z direction by the mirror 22) passes is formed in a central portion of a bottom surface of the lens barrel 100. Further, the bottom surface of the lens barrel 100 is provided with a projecting portion 100a that has the same inner diameter as that of the hole portion H4 and projects in the −Z direction with the threaded portion SR formed on its outer surface. The objective optical system 23C is fixed to the inverted microscope 20 by screwing the threaded portion SR of the projecting portion 100a to the support member (not shown). The inner diameter of the hole portion H4 formed in the lens barrel 100 is substantially the same as that of the hole portion H formed in the central portion of the concave mirror 102. Note that the shape of the lens barrel 100 is not limited to a bottomed circular annular shape, and may be another shape (for example, a bottomed square annular shape).

The glass cover 105 is a partially spherical shell-shaped member formed of, for example, glass, transparent resin or the like, and is attached to the water receiving member 106 so as to partition an internal space of the water receiving member 106 into an internal space Q1 and an internal space Q2. The glass cover 105 is firmly fixed (for example, bonded) to the water receiving member 106 so that the liquid WT held in the internal space Q1 of the water receiving member 106 does not enter the internal space Q2.

The glass cover 105 is disposed on the optical path of the pulsed light reflected by the concave mirror 102, and has an incident surface 105a on which the pulsed light reflected by the concave mirror 102 is incident, and an exit surface 105b from which the pulsed light incident from the incident surface 105a is emitted. When the liquid WT is held in the internal space Q1 of the water receiving member 106, the exit surface 105b is a liquid contact surface contacting the liquid WT. The incident surface 105a is formed so as to be orthogonal to the optical path of the pulsed light reflected by the concave mirror 102 except for the central portion. The exit surface 105b is also formed to be orthogonal to the optical path of the pulsed light reflected by the concave mirror 102. The reason for forming in this way is to prevent chromatic aberration from occurring in the wide wavelength band by preventing (as much as possible) refraction at the incident surface 105a (an interface between the air and the glass cover 105) and the exit surface 105b (an interface between the glass cover 105 and the liquid WT).

For example, the incident surface 105a of the glass cover 105 is formed into a spherical surface except for the central portion, and its center of curvature is set equal to a focal position P of a reflective objective mirror (Schwarzschild reflective objective mirror) formed by the convex mirror 101 and the concave mirror 102. The exit surface 105b of the glass cover 105 is also formed into the spherical surface, and its center of curvature is set equal to the focal position P described above. Note that a portion of the glass cover 105 through which the pulsed light transmits is a transmissive portion TS.

In the present embodiment, since the mirror holding member 104 is omitted, the convex mirror 101 is fixed to a central portion of the incident surface 105a of the glass cover 105 so that the central portion thereof is disposed on the optical axis AX, on the object side (+Z side) of the concave mirror 102. Therefore, the central portion of the incident surface 105a is made flat. The ultrasonic detector 103 is provided on the exit surface 105b of the glass cover 105 with the detection surface facing the sample SP side (+Z side). Specifically, the ultrasonic detector 103 is disposed in a concave portion 105c formed in the central portion of the exit surface 105b of the glass cover 105, and is provided on the emission surface 105b of the glass cover 105 so as to overlap the convex mirror 101 when viewed from the Z direction. As described above, the convex mirror 101 is disposed in the central portion of the incident surface 105a of the glass cover 105, and the ultrasonic detector 103 is disposed in the central portion of the exit surface 105b of the glass cover 105.

The water receiving member 106 is a tubular member having a diameter decreasing from one end portion 106a to the other end portion 106b, and the one end portion 106a is attached to an end portion on the object side of the lens barrel 100. The water receiving member 106 supports the glass cover 105 so that the internal space is partitioned into the internal space Q1 and the internal space Q2 by the glass cover 105. The water receiving member 106 can hold the liquid WT in the internal space Q1 partitioned by the glass cover 105. Further, since the diameter of the water receiving member 106 is reduced from the one end portion 106a to the other end portion 106b, even if the sample container CT1 is small, the liquid WT can be held between the sample container CT1 and the water receiving member 106. Holes portions h1 and h2 that communicate with the internal space Q1 of the water receiving member 106 and the outside of the water receiving member 106 are formed on a side surface of the water receiving member 106.

The supply tube 121 is a tube for supplying the liquid WT to the internal space Q1 of the water receiving member 106. The supply tube 121 is formed of, for example, rubber or resin, and has one end inserted into the hole portion h1 formed in the side surface of the water receiving member 106, and the other end portion connected to a liquid supply device (not shown). The liquid WT is supplied from the liquid supply device to the internal space Q1 of the water receiving member 106 through the supply tube 121. The line 103a of the ultrasonic detector 103 is drawn out of the water receiving member 106 to be connected to the controller 60, through the hole portion h2 formed in the water receiving member 106. The detection signal of the ultrasonic detector 103 is output to the controller 60 through the line 103a.

<Operation of Photoacoustic Imaging Apparatus>

The operation of the photoacoustic imaging apparatus of the present embodiment (the operation at the time of generating the fluorescence image and the operation at the time of generating the photoacoustic image) is the same as that in the first embodiment except for the operation in the inverted microscope 20. Therefore, the operation in the inverted microscope 20 will be described below. Hereinafter, in order to avoid redundant description, the operation in the inverted microscope 20 at the time of generating the fluorescence image and the operation in the inverted microscope 20 at the time of generating the photoacoustic image will be described together.

When the pulsed light emitted from the confocal unit 10 is incident on the inverted microscope 20, it is reflected in the +Z direction by the mirror 22 after passing through the imaging lens 21, and is incident on the objective optical system 23C. The pulsed light incident on the objective optical system 23C passes through the hole portion H4 formed in the lens barrel 100 and the hole H formed in the concave mirror 102, and is incident on and reflected by the convex mirror 101, and then incident on and reflected by the concave mirror 102. As shown in FIG. 12, the pulsed light reflected by the concave mirror 102 is incident on the incident surface 105a of the glass cover 105, transmits through the glass cover 105, then exits from the exit surface 105b, and passes through the liquid WT (including the liquid WT held between the water receiving member 106 and the sample container CT1) held in the internal space Q1 of the water receiving member 106, to be irradiated to the sample SP.

Here, the incident surface 105a of the glass cover 105 is formed to be orthogonal to the optical path of the pulsed light reflected by the concave mirror 102 except for the central portion. Therefore, the pulsed light reflected by the concave mirror 102 is perpendicularly incident on a peripheral portion (portion excluding the central portion) of the incident surface 105a of the glass cover 105. The exit surface 105b of the glass cover 105 is also formed to be orthogonal to the optical path of the pulsed light reflected by the concave mirror 102. Therefore, the pulsed light transmitted through the glass cover 105 is emitted in a direction perpendicular to the exit surface 105b. Therefore, the pulsed light reflected by the concave mirror 102 travels straight without being refracted by the glass cover 105.

The optical path of the pulsed light transmitted through the glass cover 105 has a refractive index close to the refractive index of the sample SP and the sample container CT1 by the liquid WT held in the internal space Q1 of the water receiving member 106 and the liquid WT held between the water receiving member 106 and the sample container CT1. Therefore, reflection of the pulsed light transmitted through the glass cover 105 (reflection at the bottom portion of the sample container CT1 and the surface of the sample SP) is extremely reduced, and a lot of pulsed light is incident on inside of the sample SP. Further, the refraction of the pulsed light transmitted through the glass cover 105 (refraction at the bottom portion of the sample container CT1 and the surface of the sample SP) is extremely reduced, and the pulsed light transmitted through the glass cover 105 travels almost straight to be condensed at the focal position P. As described above, in the objective optical system 23C of the present embodiment, since the refraction of the pulsed light hardly occurs, the pulsed light can be condensed at the original focal position P of the Schwarzschild reflective objective mirror formed by the convex mirror 101 and the concave mirror 102.

When the space between the glass cover 105 and the bottom surface of the sample container CT1 is filled with the liquid WT, since the refractive indices of the sample container CT1 and the liquid WT are close to each other, the reflection of the pulsed light is less than that in the case where it is not filled with the liquid WT (the case where it is filled with the air). However, depending on the sample container CT1 used, it is conceivable that it is difficult to make the refractive indices of the liquid WT and the sample container CT1 close to each other so that the refraction caused between the liquid WT and the sample container CT1 can be ignored. Here, as thickness of the bottom portion of the sample container CT1 is thinner, variation of the optical path due to the refraction is less, and thus it is preferable to use the sample container CT1 having a thin thickness of the bottom portion. Further, it is also preferable to incorporate an optical system for correcting the variation of the optical path, which is caused on an upper surface and a lower surface of the bottom portion of the sample container CT1, into the objective optical system 23C. For example, since the bottom surface of the sample container CT1 is often made of glass having a thickness of 0.17 mm, the concave mirror 102 configured to correct the variation of the optical path when passing through the glass may be used.

When the sample SP is irradiated with the pulsed light, fluorescence is emitted from the fluorescent substance contained in the sample SP, or the local acoustic wave is emitted from the sample SP. The fluorescence emitted from the sample SP travels in the reverse direction along the optical path of the pulsed light. As shown in FIG. 12, since the ultrasonic detector 103 is disposed on the optical axis AX, the cross-sectional shape of the fluorescence emitted from the objective optical system 23C (the shape in the plane perpendicular to the optical axis AX) is a ring shape. The local acoustic wave emitted from the sample SP passes through the sample container CT1, and then passes through the liquid WT held between the sample container CT1 and the water receiving member 106 and the liquid WT held in the internal space Q1 of the water receiving member 106, to be detected by the ultrasonic detector 103.

As described above, in the present embodiment, the objective optical system 23C is configured such that the glass cover 105 having the incident surface 105a and the exit surface 105b formed to be orthogonal to the optical path of the light reflected by the concave mirror 102 is attached to the water receiving member 106, so that the liquid WT can be held in the internal space Q1 of the water receiving member 106. Thus, since the refraction hardly occurs in the objective optical system 23C, the chromatic aberration hardly occurs. Therefore, it is possible to cope with the light in a wide wavelength range from ultraviolet light to near infrared light by one objective optical system 23C. Further, not only the chromatic aberration, but also various aberrations due to curvature can be reduced. Furthermore, in the present embodiment, since the sample SP is observed by immersion, the resolution can be improved as compared with the case of observing the sample SP without immersion.

Sixth Embodiment

<Photoacoustic Imaging Apparatus>

The overall configuration of the photoacoustic imaging apparatus of the present embodiment is the same as the overall configuration of the photoacoustic imaging apparatus 2 shown in FIG. 8. Therefore, the detailed description of the overall configuration of the photoacoustic imaging apparatus of the present embodiment will be omitted.

<Objective Optical System>

Figure 13:
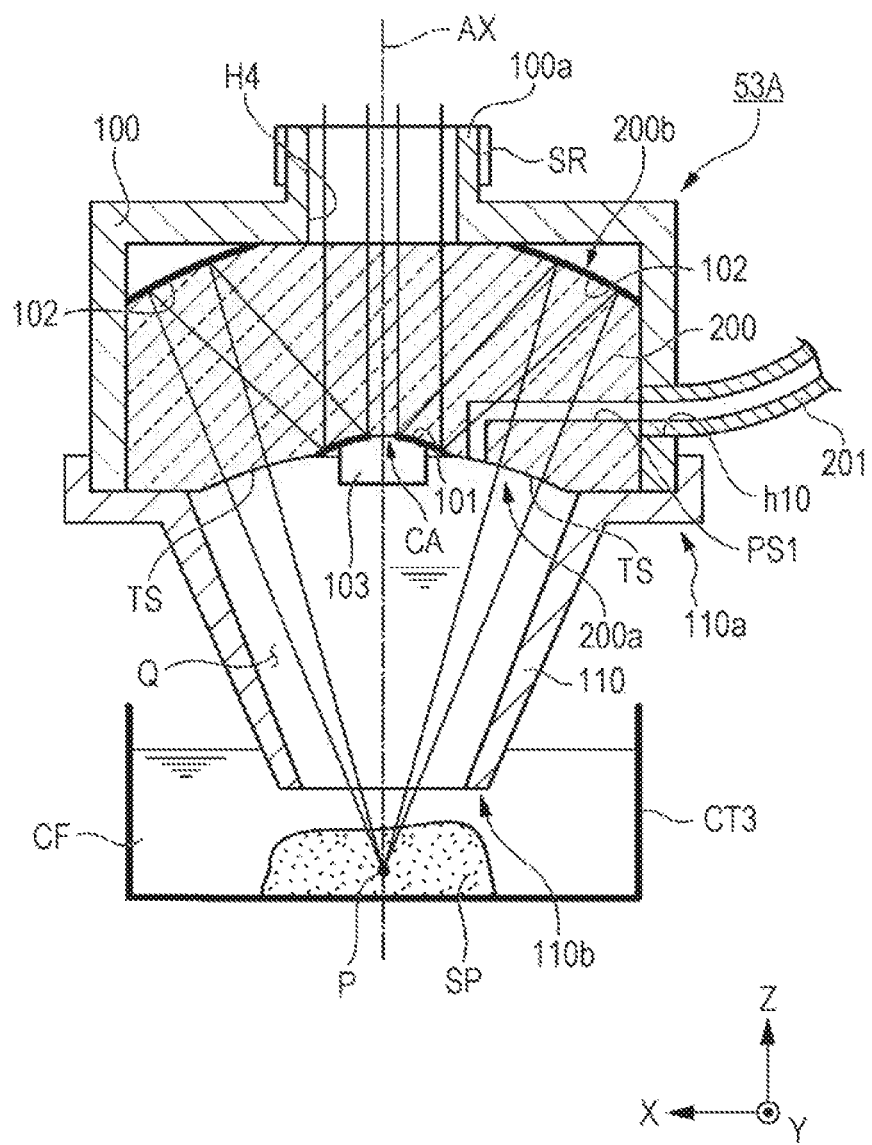
FIG. 13 is a cross-sectional view showing the main configuration of the objective optical system according to a sixth embodiment of the present invention.

FIG. 13 is a cross-sectional view showing the main configuration of the objective optical system according to a sixth embodiment of the present invention. In FIG. 13, the members corresponding to those shown in FIG. 11 are denoted by the same reference numerals. As shown in FIG. 13, the objective optical system 53A of the present embodiment is mainly different from the objective optical system 53 shown in FIG. 11 in that the lens barrel 100 is changed, the mirror holding member 104 and the glass cover 105 are omitted, an optical member 200 is provided instead of the convex mirror 101 and the concave mirror 102, and a suction tube 201 (liquid conduit) is added. The lens barrel 100 is the same as the lens barrel 100 shown in FIG. 12, however, a hole portion h10 is formed in the side surface of the lens barrel 100 of the present embodiment.

The optical member 200 is a substantially columnar member that is formed of, for example, glass, transparent resin or the like, and has one surface 200a formed in a substantially concave shape and the other surface 200b formed in a substantially convex shape. The convex mirror 101 is formed in the central portion of the one surface 200a of the optical member 200, and the transmissive portion TS is provided in a peripheral portion thereof. A central portion of the other surface 200b of the optical member 200 is formed flat, and the concave mirror 102 is formed in the peripheral portion thereof. A diameter of the central portion of the other surface 200b of the optical member 200 (a diameter of the portion formed flat) is made larger than the inner diameter of the hole portion H4 formed in the lens barrel 100.

The optical member 200 has an outer diameter substantially the same as the inner diameter of the lens barrel 100, and is held by the lens barrel 100 so that the other surface 200b is in contact with the bottom surface of the lens barrel 100 and the one surface 200a faces the object side. The optical member 200 is held such that the central portion of the other surface 200b closes the hole portion H4 formed in the lens barrel 100. Therefore, the pulsed light traveling toward the sample SP (the pulsed light reflected in the −Z direction by the mirror 52) is incident on the central portion of the other surface 200b of the optical member 200.

The convex mirror 101 formed on the one surface 200a of the optical member 200 is disposed on the optical axis AX of the pulsed light traveling toward the sample SP, and reflects the pulsed light traveling toward the sample SP. The concave mirror 102 formed on the other surface 200b of the optical member 200 reflects the pulsed light reflected by the convex mirror 101 toward the sample SP. The concave mirror 102 is designed so that the reflected pulsed light is condensed at the sample SP. The convex mirror 101 and the concave mirror 102 form the Schwarzschild reflective objective mirror.

The convex mirror 101 is formed, for example, by depositing a metal film on the central portion of the one surface 200a of the optical member 200, and the concave mirror 102 is formed, for example, by depositing the metal film on the peripheral portion of the other surface 200b of the optical member 200. The metal deposited on the optical member 200 is desirably a metal such as gold or silver having a high reflectance with respect to the light in the wide wavelength range from ultraviolet light to near infrared light.

Here, a central portion CA of the convex mirror 101 is different in that its reflectance is set lower than that of other portions of the convex mirror 101. When the light reflected by the central portion CA of the convex mirror 101 is incident on the confocal unit 40, the noise is generated. Therefore, the reflectance of the central portion CA of the convex mirror 101 is set lower than that of other portions of the convex mirror 101, so that the noise is reduced by reducing return light described above. A method of reducing the reflectance of the central portion CA of the convex mirror 101 includes, for example, a method of not depositing the metal on the central portion CA of the convex mirror 101, or of removing the metal deposited on the central portion CA of the convex mirror 101.

The transmissive portion TS provided on the one surface 200a of the optical member 200 is a portion through which the pulsed light reflected by the concave mirror 102 is transmitted. As shown in FIG. 13, the transmissive portion TS is immersed in the culture fluid CF in the sample container CT3 and thus has a liquid contact surface in contact with the culture fluid CF. The transmissive portion TS is formed orthogonal to the optical path of the pulsed light reflected by the concave mirror 102. For example, the transmissive portion TS is formed into a spherical surface, and a center of curvature thereof is set equal to the focal position P of the reflective objective mirror formed by the convex mirror 101 and the concave mirror 102. This is to prevent chromatic aberration from occurring in the wide wavelength band by preventing (as much as possible) refraction at the transmissive portion TS (an interface between the optical member 200 and the culture fluid CF). Note that a communication path PS1 communicating with the transmissive portion TS from the side surface is formed inside the optical member 200.

The ultrasonic detector 103 is provided at the central portion of the one surface 200a of the optical member 200 with the detection surface facing the sample SP side (−Z side). As shown in FIG. 13, since the ultrasonic detector 103 is attached to the surface on the −Z side of the convex mirror 101, the light transmitted through the central portion CA of the convex mirror 101 is not irradiated to the sample SP. In FIG. 13, the line connected to the ultrasonic detector 103 (the line corresponding to the line 103a in FIG. 11) and the hole portion formed in the water receiving member 110 (the hole portion corresponding to the hole portion h2 in FIG. 12) are not shown.

The suction tube 201 is a tube for supplying the liquid WT to the internal space Q of the water receiving member 110. The suction tube 201 is formed of, for example, rubber or resin, and has one end portion inserted in the hole portion h10 formed in the side surface of the lens barrel 100, and the other end portion connected to the suction pump (not shown). As shown in FIG. 13, the optical member 200 is disposed such that the communication path PS1 communicates with the hole portion h10 formed in the lens barrel 100. Therefore, by operating the suction pump (not shown), the culture fluid CF in the sample container CT3 is introduced to the internal space Q of the water receiving member 110, so that the state in which the culture fluid CF is held in the internal space Q of the water receiving member 110 (the state in which the internal space Q of the water receiving member 110 is filled with the culture fluid CF) can be achieved.

<Operation of Photoacoustic Imaging Apparatus>

The operation of the photoacoustic imaging apparatus of the present embodiment is the same as that of the third embodiment except for the operation in the upright microscope 50. Therefore, the operation in the upright microscope 50 will be described below. When the pulsed light emitted from the confocal unit 40 is incident on the upright microscope 50, it passes through the imaging lens 51 and is then reflected in the −Z direction by the mirror 52, to be incident on the objective optical system 53A.

The pulsed light incident on the objective optical system 53A passes through the hole portion H4 formed in the lens barrel 100 and is then incident on the optical member 200 from the central portion of the other surface 200b of the optical member 200. The pulsed light incident on the optical member 200 is reflected by the convex mirror 101 and then incident on and reflected by the concave mirror 102. The pulsed light reflected by the concave mirror 102 is emitted to the outside of the optical member 200 from the transmissive portion TS provided on the one surface 200a of the optical member 200. The pulsed light emitted from the optical member 200 is irradiated to the sample SP after passing through the culture fluid CF in the sample container CT3.

Here, the transmissive portion TS of the optical member 200 is formed to be orthogonal to the optical path of the pulsed light reflected by the concave mirror 102. Therefore, the pulsed light reflected by the concave mirror 102 is emitted in a direction perpendicular to the transmissive portion TS. Therefore, the pulsed light reflected by the concave mirror 102 travels straight without being refracted when being incident on the culture fluid CF from the optical member 200.

The optical path of the pulsed light emitted from the optical member 200 is set to have the refractive index close to the refractive index of the sample SP by the culture fluid CF in the sample container CT3. Therefore, the reflection of the pulsed light emitted from the optical member 200 (the reflection on the surface of the sample SP) is extremely reduced, and a lot of pulsed light is incident on the inside of the sample SP. Further, the refraction of the pulsed light emitted from the optical member 200 (the refraction at the surface of the sample SP) is also extremely reduced, and the pulsed light emitted from the optical member 200 travels almost straight to be condensed at the focal position P. As described above, the objective optical system 53A of the present embodiment also hardly refracts the pulsed light, so that the pulsed light can be condensed at the original focal point P of the Schwarzschild reflective objective mirror formed by the convex mirror 101 and the concave mirror 102.

When the pulsed light is irradiated to the sample SP, the local acoustic wave is emitted from the sample SP. The local acoustic wave emitted from the sample SP passes through the culture fluid CF and the liquid WT, held in the sample container CT3 and the internal space Q of the water receiving member 106, to be detected by the ultrasonic detector 103.

As described above, in the present embodiment, the convex mirror 101 is formed in the central portion of the one surface 200a, the concave mirror 102 is formed in the peripheral portion of the other surface 200b, and the objective optical system 53A is configured using the optical member 200 in which the transmissive portion TS formed to be orthogonal to the optical path of the light reflected by the concave mirror 102 is provided in the peripheral portion of the one surface 200a. The objective optical system 53A is used in a state where the one surface 200a of the optical member 200 is in contact with the culture fluid CF in the sample container CT3.

Therefore, since the refraction hardly occurs in the objective optical system 53A, the chromatic aberration hardly occurs. Thus, it is possible to cope with the light in the wide wavelength range from ultraviolet light to near infrared light by one objective optical system 53A. Further, not only the chromatic aberration, but also various aberrations due to the curvature can be reduced. Furthermore, in the present embodiment, since the sample SP is observed by immersion, the resolution can be improved as compared with the case of observing the sample SP without immersion.

In the present embodiment, the Schwarzschild reflective objective mirror is formed only by the optical member 200. Therefore, since the number of parts can be reduced as compared with the third embodiment, the cost can be reduced and the number of assembling steps can be reduced. Further, since the Schwarzschild reflective objective mirror is formed by depositing metal on the optical member 200, it is possible to reduce a relative positional shift between the convex mirror 101 and the concave mirror 102 due to vibration or the like compared with the first embodiment.

Seventh Embodiment

<Photoacoustic Imaging Apparatus and Operation>

The overall configuration and operation of the photoacoustic imaging apparatus of the present embodiment are the same as the overall configuration and operation of the photoacoustic imaging apparatus 1 shown in FIG. 1. Therefore, the detailed description of the overall configuration and operation of the photoacoustic imaging apparatus of the present embodiment will be omitted.

<Objective Optical System>

Figure 14:
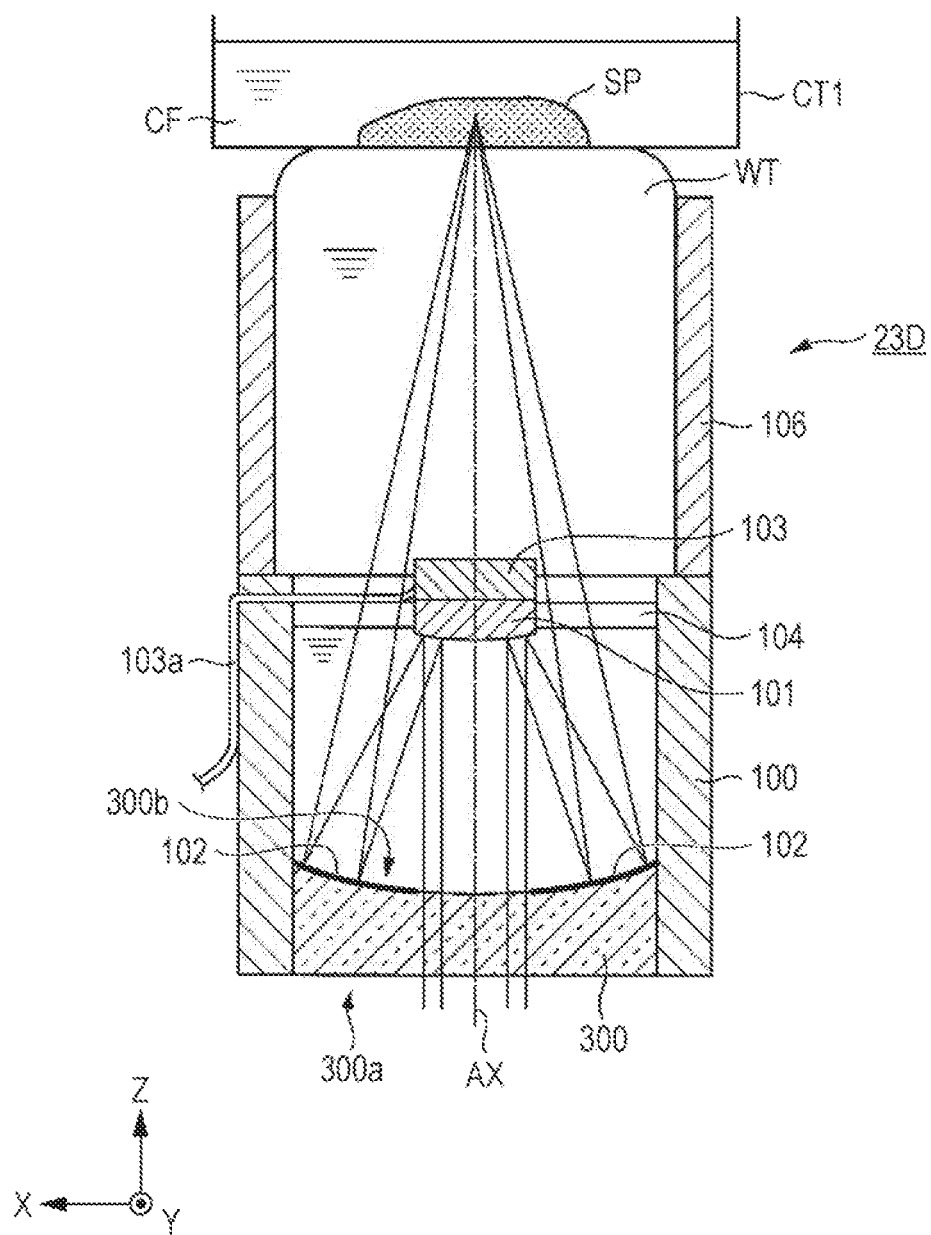
FIG. 14 is a cross-sectional view showing the main configuration of the objective optical system according to a seventh embodiment of the present invention.

FIG. 14 is a cross-sectional view showing the main configuration of the objective optical system according to a seventh embodiment of the present invention. In FIG. 14, the members corresponding to those shown in FIG. 2 are denoted by the same reference numerals. As shown in FIG. 14, the objective optical system 23D of the present embodiment is different from the objective optical system 23 shown in FIG. 2 mainly in that an optical member 300 is provided instead of the concave mirror 102, and the glass cover 105 is omitted.

The optical member 300 is a substantially columnar member that is formed of, for example, glass, transparent resin or the like, and has one surface 300a formed in a planar shape and the other surface 300b formed in a substantially concave shape. The concave mirror 102 is formed in the peripheral portion of the other surface 300b of the optical member 300. The concave mirror 102 is formed, for example, by depositing the metal film on the peripheral portion of the other surface 300b of the optical member 300. The metal deposited on the optical member 300 is desirably the metal such as gold or silver having a high reflectance with respect to the light in the wide wavelength range from ultraviolet light to near infrared light. The central portion of the other surface 300b of the optical member 300 may be a concave surface, or may be formed, for example, flat.

The optical member 300 has an outer diameter approximately equal to the inner diameter of the lens barrel 100, and is held by the lens barrel 100 so that the other surface 300b faces the object side at the other end side (−Z side) of the lens barrel 100. Therefore, the pulsed light traveling toward the sample SP (the pulsed light reflected in the +Z direction by the mirror 22 in FIG. 1) is incident on the central portion of the one surface 300a of the optical member 300. The pulsed light incident on the central portion of the one surface 300a of the optical member 300 passes through the optical member 300, and is emitted toward the +Z direction from the central portion of the other surface 300b of the optical member 300.

The concave mirror 102 formed on the other surface 300b of the optical member 300 reflects the pulsed light reflected by the convex mirror 101 toward the sample SP. The concave mirror 102 is designed so that the reflected pulsed light is condensed on the sample SP. The convex mirror 101 and the concave mirror 102 formed on the optical member 300 form the Schwarzschild reflective objective mirror.

Here, the glass cover 105 is omitted in the present embodiment. Therefore, the ultrasonic detector 103 is attached and fixed to the +Z side (object side) of the convex mirror 101 with the one end portion provided with the detection surface facing the sample SP side (+Z side). Note that, as in the first embodiment, the ultrasonic detector 103 is disposed outside the optical path of the pulsed light irradiated to the sample SP so as not to block the light irradiated to the sample SP on the +Z side of the convex mirror 101.

In the objective optical system 23D of the present embodiment, since the glass cover 105 provided in the objective optical system 23 shown in FIG. 2 is omitted, the liquid WT is held in not only the internal space of the water receiving member 106 but also the internal space of the lens barrel 100. Thus, the object side of the optical member 300 is filled with the liquid WT, and the convex mirror 101 and the concave mirror 102 are immersed in the liquid WT. In this state, since the refraction does not occur in the optical path in which the pulsed light emitted from the central portion of the other surface 300b of the optical member 300 toward the +Z direction reaches the sample container CT1, the chromatic aberration hardly occurs. Thus, it is possible to cope with the light in the wide wavelength range from ultraviolet light to near infrared light by one objective optical system 23A. Further, not only the chromatic aberration, but also various aberrations due to curvature can be reduced. Furthermore, in the present embodiment, since the sample SP is observed by immersion, the resolution can be improved as compared with the case of observing the sample SP without immersion.

The objective optical system and the photoacoustic imaging apparatus according to the embodiments of the present invention have been described above. However, the present invention is not limited to the above embodiments but can be freely changed within the scope of the present invention. For example, both the fluorescence image and the photoacoustic image can be generated in the first, second, fifth, and seventh embodiments, and in the third, fourth, and sixth embodiments, the photoacoustic imaging apparatus capable of generating only the photoacoustic image has been described as the example. However, any of the photoacoustic imaging apparatuses of the first to seventh embodiments can be designed to generate both the fluorescence image and the photoacoustic image, or can be designed to generate only the photoacoustic image. Further, the optical system 19 (see FIG. 5) in the second embodiment can also be used in the third to seventh embodiments.

In the fifth embodiment described above, the incident surface 105a (excluding the central portion) and the exit surface 105b of the glass cover 105 are formed to be orthogonal to the optical path of the laser light reflected by the concave mirror 102. In the sixth embodiment, the example in which the one surface 200a (the transmissive portion TS excluding the central portion) of the optical member 200 is formed to be orthogonal to the optical path of the pulsed light reflected by the concave mirror 102 has been described.

However, the shapes of the incident surface 105a, the exit surface 105b, and the transmissive portion TS can be changed if the refraction at the interface with the liquid WT or the like is slight and the resolution is not greatly reduced. For example, taking the glass cover 105 as an example, it is possible to change the shape of the incident surface 105a (excluding the central portion) or the exit surface 105b so that a radius of curvature r of an arbitrary point on the incident surface 105a (excluding the central portion) or the exit surface 105b satisfies a relational expression of $0.7S \leq r \leq 1.3S$, where a distance from the point to the focal position P is S. Further, the incident surface 105a (excluding the central portion) and the exit surface 105b are not limited to spherical surfaces, but may be aspherical surfaces.

LIST OF REFERENCE NUMERALS

1, 2: photoacoustic imaging apparatus, 13: scanning optical unit, 18: photodetector, 19: optical system, 19a, 19b:

axicon lens, 23: objective optical system, 23A to 23D: objective optical system, 30: controller, 53, 53A: objective optical system, 100: lens barrel, 101: convex mirror, 102: concave mirror, 103: ultrasonic detector, 103A: acoustic lens, 105: glass cover, 105a: incident surface, 105b: exit surface, 106: water receiving member, 110: water receiving member, 111: suction tube, 121: supply tube, 200: optical member, 200a: one surface, 200b: the other surface, 201: suction tube, AX: optical axis, CF: culture fluid, CT1: sample container, H: hole portion, h: hole portion, P: focal position, SP: sample, TS: transmissive portion, WT: liquid.

The invention claimed is:

1. An objective optical system, comprising:
    a first mirror having a convex reflecting surface for reflecting light traveling toward a sample;
    a second mirror having a concave reflecting surface for reflecting the light reflected by the first mirror and irradiating the sample with the light;
    a detector having at least one end portion provided on an object side of the first mirror, and detecting an acoustic wave obtained by irradiating the sample with the light;
    a lens barrel that is filled with air and is configured to support at least the second mirror therein;
    a tubular liquid holding member that is provided on an object side of the lens barrel and is configured to hold liquid therein; and
    a transparent cover member that is provided on the object side of the first mirror and the second mirror, forms a boundary surface with the liquid in the liquid holding member, and prevents the liquid from entering the first mirror and the second mirror.

2. The objective optical system according to claim 1, wherein
    a hole portion through which the light traveling toward the sample passes is formed in a central portion of the second mirror, and
    the first mirror, the second mirror, and the detector are arranged in an order of the second mirror, the first mirror, and the one end portion of the detector on an optical axis of the light traveling toward the sample.

3. The objective optical system according to claim 1, wherein
    the detector is rod-shaped, and
    a hole portion through which the detector is to be inserted is formed in a central portion of the first mirror.

4. The objective optical system according to claim 1, wherein
    the detector is disposed outside an optical path of the light irradiated to the sample so as not to block the light irradiated to the sample.

5. The objective optical system according to claim 1, wherein
    the detector comprises an acoustic lens for collecting the acoustic wave obtained by irradiating the sample with the light.

6. The objective optical system according to claim 1, wherein
    the detector is fixed to the object side of the cover member, and the first mirror is provided on an opposite side to the object side of the cover member.

7. The objective optical system according to claim 1, wherein
    at least one of a light incident surface and a light exit surface of the cover member is formed in a substantially spherical surface, and a center of curvature of the spherical surface is substantially equal to a focal position of a reflective optical system formed by the first mirror and the second mirror.

8. The objective optical system according to claim 1, wherein
    an optical path in which the light reflected by the second mirror reaches the sample or a container of the sample is filled with liquid.

9. The objective optical system according to claim 1, comprising
    an optical member having a first surface in which the first mirror is formed in a central portion thereof, and a transmissive portion is provided in a peripheral portion thereof, and a second surface in which the light traveling toward the sample is incident on a central portion thereof, and the second mirror is formed in a peripheral portion thereof, wherein
    the detector is fixed to a central portion on the object side of the optical member.

10. The objective optical system according to claim 9, wherein
    the transmissive portion is formed in a substantially spherical surface, and
    a center of curvature of the spherical surface is substantially equal to a focal position of a reflective optical system formed by the first mirror and the second mirror.

11. The objective optical system according to claim 1, comprising:
    one end portion of the liquid holding member surrounds a periphery of the object side of the lens barrel.

12. The objective optical system according to claim 1, comprising a liquid conduit for introducing the liquid into the liquid holding member.

13. The objective optical system according to claim 11, wherein
    a bottom portion of a container of the sample is disposed close to the other end portion of the liquid holding member, and
    a space between the liquid holding member and the bottom portion of the container is filled with the liquid held inside the liquid holding member.

14. The objective optical system according to claim 1, wherein
    the liquid holding member is a tubular member having a diameter reduced from the one end portion to the other end portion.

15. A photoacoustic imaging apparatus for generating an image of a sample based on an acoustic wave obtained by irradiating the sample with light, comprising
    an objective optical system comprising:
    a first mirror having a convex reflecting surface for reflecting light traveling toward a sample;
    a second mirror having a concave reflecting surface for reflecting the light reflected by the first mirror and irradiating the sample with the light;
    a detector having at least one end portion provided on an object side of the first mirror, and detecting an acoustic wave obtained by irradiating the sample with the light;
    a lens barrel that is filled with air and is configured to support at least the second mirror therein;
    a tubular liquid holding member that is provided on an object side of the lens barrel and is configured to hold liquid therein; and
    a transparent cover member that is provided on the object side of the first mirror and the second mirror, forms a boundary surface with the liquid in the liquid holding member, and prevents the liquid from entering the first mirror and the second mirror, the photoacoustic imaging apparatus irradiating the sample with light and detecting the acoustic wave obtained by irradiating the sample with the light.

16. The photoacoustic imaging apparatus according to claim 15, comprising
a scanning optical unit for scanning the light irradiated to the sample, wherein
a pupil position of the objective optical system is optically conjugated with inside or vicinity of the scanning optical unit, and
the pupil position of the objective optical system is a position of the first mirror within the objective optical system.

17. The photoacoustic imaging apparatus according to claim 15, comprising a laser light source for emitting the light; and an optical system for converting the light incident on the objective optical system into the light having a ring-shaped cross-section, wherein
the optical system is provided on an optical path between the laser light source and the objective optical system, and
the optical system is configured by using two axicon lenses arranged so that apex angles thereof are opposed to each other.

18. The photoacoustic imaging apparatus according to claim 15, further comprising:
a photodetector for detecting fluorescence obtained by irradiating the sample with the light; and
an image generator for generating a photoacoustic image based on a detection result of the acoustic wave and generating a fluorescence image based on a detection result of the photodetector.

19. The objective optical system according to claim 1, comprising: wherein
the tubular liquid holding member has one end portion provided on one end side of the lens barrel and the other end portion disposed close to a bottom portion of a sample container storing the sample, and
the transparent cover member is surrounded by the liquid holding member.

20. A photoacoustic imaging apparatus for generating an image of a sample based on an acoustic wave obtained by irradiating the sample with light, comprising
a laser light source for emitting the light;
an objective optical system comprising:
a first mirror having a convex reflecting surface for reflecting light traveling toward a sample;
a second mirror having a concave reflecting surface for reflecting the light reflected by the first mirror and irradiating the sample with the light;
a detector having at least one end portion provided on an object side of the first mirror, and detecting an acoustic wave obtained by irradiating the sample with the light; and
a transparent cover member that is provided on the object side of the first mirror and the second mirror, forms a boundary surface with liquid, and prevents the liquid from entering the first mirror and the second mirror; and
an optical system for converting the light incident on the objective optical system into the light having a ring-shaped cross-section, wherein
the optical system is provided on an optical path between the laser light source and the objective optical system,
the optical system is configured by using two axicon lenses arranged so that apex angles thereof are opposed to each other, and
the photoacoustic imaging apparatus irradiating the sample with light and detecting the acoustic wave obtained by irradiating the sample with the light.

* * * * *